United States Patent
Soederstroem et al.

(10) Patent No.: US 9,512,228 B2
(45) Date of Patent: Dec. 6, 2016

(54) SELECTIVE ELIMINATION OF EROSIVE CELLS

(75) Inventors: Kalle Soederstroem, London (GB); Elisabeth Douglas Galsgaard, Naerum (DK)

(73) Assignee: NOVO NORDISK A/S, Bagsvaerd (DK)

(*) Notice: Subject to any disclaimer, the term of this patent is extended or adjusted under 35 U.S.C. 154(b) by 0 days.

(21) Appl. No.: 14/124,876

(22) PCT Filed: Jun. 18, 2012

(86) PCT No.: PCT/EP2012/061583
§ 371 (c)(1),
(2), (4) Date: Feb. 24, 2014

(87) PCT Pub. No.: WO2012/172102
PCT Pub. Date: Dec. 20, 2012

(65) Prior Publication Data
US 2014/0161802 A1    Jun. 12, 2014

Related U.S. Application Data

(60) Provisional application No. 61/501,533, filed on Jun. 27, 2011.

(30) Foreign Application Priority Data

Jun. 17, 2011 (EP) .................... 11170402

(51) Int. Cl.
*A61K 39/395* (2006.01)
*C07K 16/28* (2006.01)

(52) U.S. Cl.
CPC ....... *C07K 16/2851* (2013.01); *C07K 16/2803* (2013.01)

(58) Field of Classification Search
None
See application file for complete search history.

(56) References Cited

U.S. PATENT DOCUMENTS

| | | | |
|---|---|---|---|
| 5,489,525 A | 2/1996 | Pastan | |
| 5,859,205 A * | 1/1999 | Adair et al. | 530/387.3 |
| 5,876,950 A | 3/1999 | Siadak et al. | |
| 5,994,524 A | 11/1999 | Matsushima et al. | |
| 8,206,709 B2 | 6/2012 | Spee et al. | |
| 8,796,427 B2 | 8/2014 | Spee et al. | |
| 2003/0095965 A1 | 5/2003 | Van Beneden et al. | |
| 2003/0171280 A1 | 9/2003 | Soderstrom | |
| 2005/0037002 A1 | 2/2005 | Velardi et al. | |
| 2009/0208416 A1 | 8/2009 | Moretta et al. | |
| 2011/0052606 A1 | 3/2011 | Spee et al. | |
| 2011/0229486 A1 | 9/2011 | Moretta et al. | |

FOREIGN PATENT DOCUMENTS

| | | |
|---|---|---|
| CN | 1747969 A | 3/2006 |
| CN | 101107269 A | 1/2008 |
| EP | 1036327 A2 | 9/2000 |
| JP | 03112485 A | 5/1991 |
| JP | 03112486 A | 5/1991 |
| JP | 03112487 A | 5/1991 |
| JP | 2004-528824 A | 9/2004 |
| JP | 03112484 U | 8/2005 |
| WO | 99/28748 A2 | 6/1999 |
| WO | 01/71005 A2 | 9/2001 |
| WO | 02/05122 | 1/2002 |
| WO | 02/50122 | 6/2002 |
| WO | 03/008449 A1 | 1/2003 |
| WO | 03/095965 A2 | 11/2003 |
| WO | 2004/003019 A2 | 1/2004 |
| WO | 2004/056312 | 7/2004 |
| WO | 2005/009465 A1 | 2/2005 |
| WO | 2005/105849 A1 | 11/2005 |
| WO | 2006/070286 | 7/2006 |
| WO | 2007042573 A2 | 4/2007 |
| WO | WO 2007042573 A2 * | 4/2007 |
| WO | 2008/009545 | 1/2008 |
| WO | WO 2008009545 A1 * | 1/2008 |
| WO | 2009/092805 A1 | 7/2009 |
| WO | WO 2011/104381 | 9/2011 |

OTHER PUBLICATIONS

Vajdos et al. (J Mol Biol. Jul. 5, 2002;320(2):415-28).*
Rudikoff et al. (Proc. Natl. Acad. Sci. USA, 79: 1979-1983, Mar. 1982).*
Colman (Research in Immunology, 145:33-36, 1994).*
Brown et al. (J Immunol. May 1, 1996;156(9):3285-91).*
Eduardo Padlan, Mol Immunol. Feb. 1994;31(3):169-217.*
Portolano et al., J Immunol. Feb. 1, 1993;150(3):880-7.*
Aramaki et al. (Mod Rheumatol (2009) 19:245-252).*
Huss et al. (Arthritis & Rheumatism, vol. 62, No. 12, Dec. 2010, pp. 3799-3805).*
Schett, Ann Rheum Dis 2007;66(Suppl III):iii42-iii44.*
Dankbar et al., J Orthop Res 25:569-577, 2007.*
Bagot et al., "Functional Inhibitory Receptors Expressed by a Cutaneous T-Cell Lymphoma-Specific Cytolytic Clonal T-Cell Population," Journal of Investigative Dermatology, 2000, vol. 115, No. 6, pp. 994-999.
Bagot et al., "CD4+ Cutaneous T-Cell Lymphoma Cells Express the p140-Killer Cell Immunoglobulin-like Receptor," Blood, 2001, vol. 97, No. 5, pp. 1388-1391.
Biassoni et al., "Molecular and Functional Characterization of NKG2D, NKp80, and NKG2C Triggering NK Cell Receptors in Rhesus and Cynomolgus Macaques: Monitoring of NK Cell Function During Simian HIV Infection," Journal of Immunology, 2005, vol. 174, pp. 5695-5705.
Carretero et al., "The CD94 and NKG2-A C-type Lectins Covalently Assemble to Form a Natural Killer Cell Inhibitory Receptor for HLA Class I Molecules," European Journal of Immunology, 1997, vol. 27, pp. 563-567.
Costa et al., "Differential Disappearance of Inhibitory Natural Killer Cell Receptors during HAART and Possible Impairment of HIV-1-Specific CD8 Cytotoxic T Lymphocytes," AIDS, 2001, vol. 15, pp. 965-974.

(Continued)

*Primary Examiner* — Zachary Skelding
(74) *Attorney, Agent, or Firm* — Saliwanchik, Lloyd & Eisenschenk

(57) ABSTRACT

The current invention relates to the treatment of diseases characterized by cartilage destruction and/or bone erosion. In particular the present invention relates to the treatment of osteoarthritis, osteoporosis, psoriatic arthritis or rheumatic arthritis with an anti-NKG2A antibody.

19 Claims, 29 Drawing Sheets

(56) References Cited

OTHER PUBLICATIONS

Haedicke et al., "Expression of CD94/NKG2A and Killer Immunoglobulin-Like Receptors in NK Cells and a Subset of Extranodal Cytotoxic T-cell Lymphomas," Blood, 2000, vol. 95, No. 11, pp. 3628-3630.
Kamarashev et al., "Differential Expression of Cytotoxic Molecules and Killer Cell Inhibitory Receptors in CD8+ and CD56+ Cutaneous Lymphomas," American Journal of Pathology, 2001, vol. 158, No. 5, pp. 1593-1598.
Le Bouteiller et al., "Engagement of CD160 Receptor by HLA-C is a Triggering Mechanism used by Circulating Natural Killer (NK) Cells to Mediate Cytotoxicity," Proceedings of the National Academy of Sciences in the USA, 2002, vol. 99, No. 26, pp. 16963-16968.
Mavilio et al., "Identification of NKG2A and NKp80 as Specific Natural Killer Cell Markers in Rhesus and Pigtailed Monkeys," Blood, 2005, vol. 106, No. 5, pp. 1718-1725.
Mingari et al., "HLA Class I-specific Inhibitory Receptors in Human T Lymphocytes: Interleukin 15-induced Expression of CD94/NKG2A in Superantigen- or Alloantigen-activated CD8+ T Cells," Proceedings of the National Academy of Sciences of the USA, 1998, vol. 95, pp. 1172-1177.
Ponte, et al., "Inhibitory Receptors Sensing HLA-G1 Molecules in Pregnancy: Decidua-associated Natural Killer Cells Express LIR-1 and CD94/NKG2A and Acquire p49, and HLA-G1-Specific Receptor," Proceedings of the National Academy of Sciences of the USA, 1999, vol. 96, pp. 5674-5679.
Petrie, E. J., et al. CD94-NKG2A recognition of human leukocyte antigen (HLA)-E bound to an HLA class I leader sequence (2008), J. Exp. Med. 205; 725-735.
Sivori et al., "p46, a Novel Natural Killer Cell-specific Surface Molecule that Mediates Cell Activation," Journal of Experimental Medicine, 1997, vol. 186, No. 7, pp. 1129-1136.
Vacca et al., "Analysis of Natural Killer Cells Isolated from Human Decidua: Evidence that 2B4 (CD244) Functions as an Inhibitory Receptor and Blocks NK-cell Function," Blood, 2006, vol. 108, No. 13, pp. 4078-4085.
Vitale et al., "The Leukocyte Ig-like Receptor (LIR)-1 for the Cytomegalovirous UL18 Protein Displays a Broad Specificity for Different HLA Class I Alleles: Analysis of LIR-1+ NK Cell Clones," International Immunology, 1999, vol. 11, No. 1, pp. 29-35.
Voss et al., "Participation of the CD94 Receptor Complex in Costimulation of Human Natural Killer Cells," Journal of Immunology, 1998, vol. 160, pp. 1618-1626.
Zimmer et al., "Activity and Phenotype of Natural Killer Cells in Peptide Transporter (TAP)-deficient Patients (Type I Bare Lymphocyte Syndrome)," Journal of Experimental Medicine, 1998, vol. 187, No. 1, pp. 117-122.
Castriconi et al., "Shaping of Adaptive Immunity by Innate Interactions," C.R. Biologies, 2004, vol. 327, pp. 533-537.
Guma et al., "Imprint of Human Cytomegalovirus Infection on the NK Cell Receptor Repertoire," Blood, 2004, vol. 104, No. 12, pp. 3664-3671.
Gunturi et al., "The Role of CD94/NKG2 in Innate and Adaptive Immunity," Immunologic Research, 2004, vol. 30, No. 1, pp. 29-34.
Jinushi et al., "Negative Regulation of NK Cell Activities by Inhibitor Receptor CD94/NKG2A Leads to Altered NK Cell-Induced Modulation of Dendritic Cell Functions in Chronic Hepatitis C Virus Infection," The Journal of Immunology, 2004, vol. 173, pp. 6072-6081.
Llano et al., "Differential Effects of US2, US6, and US11 Human Ctyomegalovirus Proteins on HLA Class Ia and HLA-E Expression: Impact on Target Susceptibility to NK Cell Subsets," European Journal of Immunology, 2003, vol. 33, pp. 2744-2754.
Riteau et al., "HLA-G1 Co-Expression Boosts the HLA Class I-Mediated NK Lysis Inhibition," International Immunology, 2001, vol. 13, No. 2, pp. 193-201.
Ward et al., HLA-C and HLA-E Reduce Antibody-Dependent Natural Killer Cell-Mediated Cyotoxicity of HIV-Infected Primary T Cell Blasts, AIDS, 2004, vol. 18, pp. 1769-1779.

Pedersen et al., "Differential Expression of Inhibitory or Activating CD94/NKG2 Subtypes on MART-1-Reactive T Cells in Vitiligo Versus Melanoma: A Case Report," J. Invest. Derm., 2002, vol. 118, pp. 595-599.
Wu M Anna et al., "Multimerization of a chimeric anti-CD20 single-chain Fv-Fc fusion protein is mediated through variable domain exchange," Prot. Engin., 2001, vol. 14, pp. 1025-1033.
Author Guide, Blood, pp. 1-19, Aug. 30, 2010.
Instructions to Authors, European Journal of Immunology, pp. 1-6, 2009.
Gavilondo et al., "Antibody Engineering at the Millennium," Biotechniques, 2000, vol. 29, No. 1, pp. 128-145.
Moretta et al., Identification of Four Subsets of Human CD3-CD16+ Natural Killer (NK) Cells by the Expression of Clonally Distributed Functional Surface Molecules: Correlation between Subset Assignment of NK Clones and Ability to Mediate Specific Alloantigen Recognition, J. Exp. Med., 1990, vol. 172, pp. 1589-1598.
Cleland et al., "The Development of Stable Protein Formulations: A Close Look at Protein Aggregation, Deamidation, and Oxidation," Critical Reviews in Therapeutic Drug Carrier Systems, 1993, vol. 10, No. 4, pp. 307-377.
Sablitzky et al., "Molecular Basis of an Isogenic Anti-Idiotypic Response," The EMBO Journal, 1984, vol. 3, No. 12, pp. 3005-3012.
Casset et al., Biochemical and Biophysical Research Communications, "A Peptide Mimetic of an Anti-CD4 Monoclonal Antibody by Rational Design", 2003, vol. 307, pp. 198-205.
Chen et al., Journal of Molecular Biology., "Selection and Analysis of an Optimized Anti-VEGF Antibody: Crystal Structure of an Affinity-Matured FAB in Complex With Antigen", 1999, vol. 293, pp. 865-881.
De Pascalis et al., Journal of Immunology, "Grafting of "Abbreviated" Complementarity-Determining Regions Containing Specificity-Determining Residues Essential for Ligand Contact to Engineer a Less Immunogenic Humanized Monoclonal Antibody", 2002, vol. 169, pp. 3076-3084.
Gonzales Noreen E et al, Tumor Biology, "Minimizing the Immunogenicity of Antibodies for Clinical Application", 2005, vol. 26, No. 1, pp. 31-43.
Holm et al., Molecular Immunology, "Functional Mapping and Single Chain Construction of the Anti-Cytokeratin 8 Monoclonal Antibody TS1", 2007, vol. 44, pp. 1075-1084.
Kashmiri et al., Methods, "SDR Grafting—A New Approach to Antibody Humanization", 2005, vol. 36, No. 1, pp. 25-34.
Kumar et al., Journal of Biological Chemistry, "Molecular Cloning and Expression of the FABS of Human Autoantibodies in *Escherichia coli*", 2000, vol. 275, pp. 35129-35136.
MacCallum et al., Journal of Molecular Biology., "Antibody-Antigen Interactions: Contact Analysis and Binding Site Topography", 1996, vol. 262, pp. 732-745.
Rudikoff et al., Proceedings of the National Academy of Sciences of the USA, "Single Amino Acid Substitution Altering Antigen-Binding Specificity", 1982, vol. 79, pp. 1979-1983.
Smith-Gill et al., Journal of Immunology, "Contributions of Immunoglobulin Heavy and Light Chains to Antibody Specificity for Lysozyme and Two Haptens", 1987, vol. 139, pp. 4135-4144.
Song et al., Biochemical and Biophysical Research Communications, "Light Chain of Natural Antibody Plays a Dominant Role in Proten Antigen Binding", 2000, vol. 268, pp. 390-394.
Vajdos et al., Journal of Molecular Biology., "Comprehensive Functional Maps of the Antigenbiding Site of an Anti-ERBB2 Antibody Obtained With Shotgun Scanning Mutagenesis", 2002, vol. 320, pp. 415-428.
Ward et al., Nature, "Binding Activities of a Repertoire of Single Immunoglobulin Variable Domains Secreted From *Escherichia coli*", 1989, vol. 341, pp. 544-546.
Wu H. et al., Journal of Molecular Biology, "Humanization of a Murine Monoclonal Antibody by Simultaneous Optimization of Framework and CDR Residues", 1999, vol. 294, No. 1, pp. 151-162.
Gessner et al., "The IgG Fc receptor family," 1998, Ann Hematol, vol. 76, pp. 231-248.

(56) References Cited

OTHER PUBLICATIONS

Reddy et al., "Elimination of Fc Receptor-Dependent Effector Functions of a Modified IgG4 Monoclonal Antibody to Human CD4," 2000, J. Immunol, vol. 164, pp. 1925-1933.
Yokoyama et al., "Immune functions encoded by the natural killer gene complex," 2003, Nature Rev Immunol, vol. 3, pp. 304-316.
Fauser, A. A. et al. "Guidelines for Anti-emetic Therapy: Acute Emesis" Eur. J Canc., 1999, pp. 361-370, vol. 35. No. 3.
Downs, S et al. "Development of Antibodies Specific for NKG2 Family Members." 2011. Depts. of Monoclonal Antibodies and antibody applications,R&D Systems Inc,Minneapolis MN,USA.
Sharma et al., The Journal of Pharmacology and Experimental Therapeutics, "Comparative Pharmacodynamics of Keliximab and Clenoliximab in Transgenic Mice Bearing Human CD4", 2000, vol. 293, No. 1, pp. 33-41.
Carter, P. et al., "Humanization of an Anit-P185 Antibody for Human Cancer Therapy," Preceedings of the National Academy of Science of the USA, 1992, vol. 89, No. 10, pp. 4285-4289.
Mocikat R. et al., Immunity, "Natural Killer Cells Activated by MHC Class ILow Targets Prime Dendritic Cells to Induce Protective CD8 T Cell Responses", 2003, vol. 19, No. 4, pp. 561-569.
O'Neill et al., Blood, "Manipulating Dendritic Cell Biology for the Active Immunotherapy of Cancer", 2004, vol. 104, No. 8, pp. 2235-2246.
Ohlen C et al., Science, "Prevention of Allogeneic Bone Marrow Graft Rejection by H-2 Transgene in Donor Mice", 1989, vol. 246, No. , pp. 666-668.
Derre et al., Journal of Immunology, vol. 177, pp. 3100-3107 (2006).
Carretero M et al., European Journal of Immunology, "Specific Engagement of the CD94/NKG2-A Killer Inhibitory Receptor by the HLA-E Class Ib Molecule Induces SHP-1 Phosphatase Recruitment to Tyrosine-Phosphorylated NKG2-A: Evidence . . . ", 1998, vol. 28, No. 4, pp. 1280-1291.
Casadevall A et al., Nature Reviews Microbiology, "Passive Antibody Therapy for Infectious Diseases", 2004, vol. 2, No. 9, pp. 695-703.
Coiffier B et al, The Hematology Journal, "Dose Intensity or Monoclonal Antibody I First-Line Treatment", 2004, vol. 5, No. -, pp. S154-S158.
Fang M et al., Immunity, "CD94 Is Essential for NK Cell-Mediated Resistance to a Lethal Viral Disease", 2011, vol. 34, No. , pp. 579-589.
Gatto et al., Current medical Chemistry-Anti Cancer Agents, "Mono Clonal Antibodies Cancer Therapy", 2004, vol. 4, No. 5, pp. 411-414.
Hinoda et al., Cancer Science, "Monoclonal Antibodies as Effective Therapeutic Agents for Solid Tumors", 2004, vol. 95, No. 8, pp. 621-625.
Kaiser B K et al., Journal of Immunology, "Interactions Between NKG2X Immunoreceptors and HLA-E Ligands Display Overlapping Affinities and Thermodynamics", 2005, vol. 174, No. 5, pp. 2878-2884.
Kärre, K et al., Nature, "Selective Rejection of H-2-Deficient Lymphoma Variants Suggests Alternative Immune Defence Strategy", 1986, vol. 319, No. , pp. 675-678.
Ludewig B et al., Immunological Reviews., "Role of Dendritic Cells in the Induction and Maintenance of Autoimmune Diseases", 1999, vol. 169, No. , pp. 45-54.
Coupel et al., Blood, vol. 109, pp. 2806-2814 (2007).
Martin et al., Immunogenetics, "The Genomic Organization and Evolution of the Natural Killer Immunoglobulin-Like Receptor (KIR) Gene Cluster", 2000, vol. 51, No. -, pp. 268-280.
Miller et al., Blood, "Human Natural Killer Cells With Polyclonal Lectin and Immunoglobulinlike Receptors Develop From Single Hematopoietic Stem Cells With Preferential Expression of NKG2A and KIR2DL2/L3/S2", 2001, vol. 98, No. 3, pp. 705-713.
Olszewski A j et al., Science STKE, "Empowering Targeted Therapy: Lessons From Rituximab", 2004, vol. 241, No. , pp. 1-6.

Borrego et al. "The CD94/NKG2 Familty of Receptors," Imm. Res., 2006, vol. 35, No. 3, pp. 263-277.
Yawata M et al., Critical Reviews in Immunology, "Variation Within the Human Killer Cell Immunoglobulin-Like Receptor(KIR) Gene Family", 2002, vol. 22, No. 5&6, pp. 463-482.
Aldrich et al., "Identification of Tap-Dependent Leader Peptide Recognized by Alloreactive T Cells Specific for a Class Ib Antigen," Cell, 1994, vol. 79, pp. 649-658.
Aramburu et al., "A Novel Function Cell Surface Dimer (Kp43) Expressed by Natural Killer Cells and T Cell Receptor-Gamma/Delta+ T Lymphocytes," The Journal of immunology, 1990, vol. 144, No. 8, pp. 3238-3247.
Borrego, Francisco et al., "Recognition of Human Histocompatability Leukocyte Antigen (HLA)-E Complexed with HLA Class I Signal Sequence-Derived Peptides by CD94/NKG2 Confers Protection from Natural Killer Cell-Mediated Lysis", Journal of Experimental Medicine, Mar. 2, 1998, vol. 187, No. 5, pp. 813-881.
Braud et al, TAP-and tapasin-dependent HLA-E Surface Expression Correlates with the Binding of an MHC Class Leader Peptide, Current Biology, 1998, vol. 8, No. 1, pp. 1-10.
Braud et al., "The Human Major Histocompatibility Complex Class Ib Molecule HLA-E Binds signal Sequence-derived Peptides with Primary Anchor Residues at Position 2 and 9," Eur. J. Immunol., 1997, vol. 27, pp. 1164-1169.
Mingari, M.C et al., International Immunology, "Cytolytic I Lymphocytes Displaying Naturla Killer . . . ", 1995, vol. 7, No. 4, pp. 697-703.
Roque et al. Biotechnology Progress. "Antibodies and Genetically Engineered Related Molecules" 2004 vol. 20(3) pp. 639-654.
Houchins et al., "DNA Sequence Analysis of NKG2, a Family of Related cDNA Clones Encloding Type II Integral Membrane Proteins on Human Natural Killer Cells", J. Exp. Med., 1991, vol. 173, pp. 1017-1020.
Houchins et al., Natural Killer Cell Cytolytic Activity is Inhibited by NKG2-A and Activated by NKG2-C, The Journal of Immunology, 1997, vol. 158, pp. 3603-3609.
Lanier et al., "Arousal and Inhibition of Human NK Cells," Immunological Reviews, 1997, vol. 155, pp. 145-154.
Lanier et al., Immunoreceptor DAP12 Bearing a Tyrosine-Based Activation Motif is Involved in Activiating NK Cells, Nature 1998, vol. 391, pp. 703-707.
Lazetic et al., "Human Natural Killer Cell Receptors Involved in MHC Class I Recognition are Disulfide-Linked Heterokimers of CD94 and NKG2 Subunits," The Journal of Immunology, 1996, vol. 157, pp. 4741-4745.
Lee et al., "HLA-E Surface Expression Depends on Binding of Tap-Dependent Peptides Derived from Certain HLA Class I Signal Sequences," The Journal of Immunology, 1998, vol. 160, pp. 4951-4960.
Leibson, Paul J., "Cytotoxic Lymphocyle Recognition of HLA-E: Utilizing a Nonclassical Window to Peer into Classical MHC," Immunity, 1998, vol. 9, No. 3, pp. 289-294.
Llano et al., "HLA-EBound Peptides Influence Recognition by Inhibitory and Triggering CD94/NKG2 Receptors, Preferential Response to an HLQ-G Derived Nonamer," European Journal Immunology, 1998, vol. 29, No. 9, pp. 2854-2863.
O'Callaghan et al., "Structure and Funtion of the Human MHC Class Ib Molecules HLA-E, HLA-F and HLA-G," Immunol. Rev., 1998, vol. 163, pp. 129-138.
O'Callaghan et al., Structural Features Impose Tight Peptides Binding Specifically in teh Nonclassical MHC Molecule HLA-E, Molecular Cell, 1998, vol. 1, No. 4, pp. 531-541.
Perez-Villar et al., "Functional Ambivalence of the Kp43 (CD 94) NK Cell-Associated Surface Antigen," the Journal of Immunology, 1995, vol. 154, pp. 5779-5788.
Phillips et al., "CD94 and a Novel Associated Protein (94AP) Form a NK Cell Receptor Involved in the Recognition of HLA-A, HLA-B and HLA-C Allotypes," Immunity, 1996, vol. 5, pp. 163-172.
Plougastel et al., "Cloning of NKG2-F, a New Member of the NKG2 Family of Human Natural Killer Cell Receptor Genes," Eur. J. Immunol., 1997, vol. 27, pp. 2835-2839.

(56) References Cited

OTHER PUBLICATIONS

Posch et al., "HLA-E is the Ligand for the Natural Killer Cell CD94/NK02 Receptors," Journal of Biomedical Science, 1998, vol. 5, No. 5, pp. 321-331.
Shawar et al., "Antigen Presentation by Major Histocompatibility Complex Class I-B Molecules," Annual Review of Immunology, 1994, vol. 12, pp. 839-880.
Sivori et al., "Inhibitory CD94 Molecules Identified by the Z199 Monoclonal Antibody Recognize Different HLA-Class I Molecules," Transplantation Proceedings, 1996, vol. 28, No. 6, pp. 3199-3203.
Ulbrecht et al., "The HLA-E Gene Encodes Two Differently Regulated Transcripts and a Cell Surface Protein," The Journal of Immunoloty, 1992, vol. 149, No. 9, pp. 2945-2953.
Ulbrecht et al., "Impaired Intracellular Transport and Cell Surface Expression of Nonpolymorphic HLA-E Evidence for Inefficient Peptide Building," J Exp Med, 1992, vol. 176, pp. 1083-1090.
Marshak-Rothstein et al., "Hybridoma proteins expressing the predominant idiotype of the antiazophenylarsonate response of A/J mice," PNAS, 1980, vol. 77, pp. 1120-1124.
Casadevall A. et al., "Immunoglobulin Isotype Influences Affinity and Specificity," Proc Natl Acad Sci USA, 2012, vol. 109, No. 31, pp. 12272-12273.
Biochemistry, "http://bochemistry.ru/biohimija_severina/b5873content.html", 2003.
Roit et al., New methods of Immunoassay, 1991, pp. 65-75.
Roitt et al, Immunology, 2000, pp. 106-111.
Roitt et al, Immunology, 2000, pp. 530-535.
Singer et al., Genes and Genomes, 1998, vol. 1, pp. 63.
NCBI Database, "Gene Bank IDS GI:20981680", dated Apr. 3, 2013.
NCBI Database, "Gene Bank IDS GI:116013", dated May 29, 2013.
Paul, Fundamental Immunology, 3rd Edition, 1993, pp. 292-295.
Brown et al, J. Immunol. 1996; 156(9):3285-91.
Demotte et al. Eur. J. Immunol. vol. 32: p. 1688-1697, 2002.
Vitale et al, 2004, J. Exp. Med. vol. 34: p. 455-460.
Bottino et al. 2001. J. Exp. Med. vol. 194: p. 235-246.
PNAS information for Authors, 2013, p. i-iv.
Mavillio et al. Nov. 2003, PNAS vol. 100: p. 15011-15016.
Soderstrom et al. CD94/NKG2 is the Predominant Inhibitory. J of Immunology. 1997 vol.159 pp. 1072-1075, Abstract.
Le Bouteiller et al., Research in Immunology, "Antigen-Presenting Function(s) of the Non-Classical HLA-E,-F and -G Class I Molecules: The Beginning of a Story", 1996, vol. 147, No. 5, pp. 301-313.
D'Andrea, A. et al. "Regulation of T cell Lymphokine Production by killer Cell Inhibitory Receptor Recognition of Self HLA Class I Alleles," J. Exp. Med., Aug. 1996, pp. 789-794, vol. 184.
Pende, D. et al. "HLA-G recognition by human natural killer cells. Involvement of CD94 both as inhibitory and as activating receptor complex," Eur. J. Immunol., 1997, pp. 1875-1880, vol. 27.
Perez-Villar, J. J. et al. "The CD94/NKG2-A Inhibitory Receptor Complex is Involved in Natural Killer Cell-Mediated Recognition of Cells Expressing HLA-G1," The Journal of Immunology., Mar. 14, 1997, pp. 5736-5743, vol. 158.
Presta, L.G. "Engineering of therapeutic antibodies to minimize immunogenicity and optimize function," Advanced Drug Delivery Reviews, 2006, pp. 640-656, vol. 58, No. 5-6.
Durand, M., et al., "Monocytes From Patients With Osteoarthritis Display Increased Osteoclastogenesis and Bone Resorption," Arthritis & Rheumatism, Jan. 2013, vol. 65, No. 1, pp. 148-158.
Isaacs, J.D., et al., "Therapeutic agents for patients with rheumatoid arthritis and an inadequate response to tumour necrosis factor-α antagonists," Expert Opinion on Biological Therapy, 2009, vol. 9, No. 12, pp. 1463-1475.
Liao, K.P., et al., "Clinical predictors of erosion-free status in rheumatoid arthritis: a prospective cohort study," Rheumatology Advance Access, Mar. 29, 2011, pp. 1-7.
Saleem, B., et al., "Patients with RA in remission on TNF blockers: when and in whom can TNF blocker therapy be stopped?," Annals of the Rheumatic Diseases, 2010, vol. 69, pp. 1636-1642.
Zwerina, J. et al. "Single and Combined Inhibition of Tumor Necrosis Factor, Interleukin-1, and RANKL Pathways in Tumor Necrosis Factor—Induced Arthritis" Arthritis and Rheumatism, Jan. 2004, pp. 277-290, vol. 50, No. 1.
Braud et al., HLA-E bindsto natural killer cell receptors CD94/NKG2A, B and C, "Nature", Year 1998, vol. 391, pp. 795-799.
Brooks et al.,Specific Recognition of HLA-E, But Not Classical, HLA Class I; Molecules by Soluble CD94/NKG2A and NK Cells, "Journal of Immunology", Year 1999, vol. 162, pp. 305-313.
Brooks et al.NKG2A Complexed with CD94 Defines a Novel Inhibitory; Natural Killer Cell Receptor, "Journal for Expieremental Medicine", Year 1997, vol. 185, pp. 795-800.
C. Priggeon et al. Natural killer cells in the synovial fluid of rheumatoid arthritis patients exhibit a CD56bright, CD94bright,CD158negative phenotype, "Rheumatology", Year 2003, vol. 42, No. 7, pp. 870-878.
Cooper M A et al. NK cell and DC interactions,"Trends in Immunology" Year 2004, vol. 25, No. 1, pp. 47-52.
Cristina Teixeira De Matos et al. Activating and inhibitory receptors on synovial fluid natural killercells of arthritis patients: role of CD94/NKG2A in control of cytokine secretion,"Imunology", Year 2007, vol. 122, No. 2, pp. 291-301.
J.W. Leavenworth et al. Mobilization of natural killer cells inhibits development of collagen-induced arthritis,"Proceedings of the National Academy of sciences", Year 2011, vol. 108, No. 35, pp. 14584-14589.
K.S. Park et al.Inhibitory NKG2A and activating NKG2D and NKG2C natural killer cell receptor genes: susceptibility for rheumatoid arthritis. "Tissue Antigens", Year 2008, vol. 72, No. 4, pp. 342-346.
Lee et al., HLA-E is a major ligand for the natural killer inhibitory receptor; CD94yNKG2A, "PNAS" Year 1998, vol. 95, pp. 5199-5204.
Lu et al. Regulation of Activated CD4+ T Cells by NK Cells; via the Qa-1-NKG2A Inhibitory Pathway, "Immunity", Year 2007, vol. 26, pp. 593-604.
Miller et al.,Analysis of HLA-E Peptide-Binding Specificityand Contact Residues in Bound Peptide Required for Recognition by CD94/NKG2,"Joumal for Immunology", Year 2003, vol. 171, pp. 1369-1375.
Moretta et al. HLA class I specific inhibitory receptors, "Current Opinion Immunology", Year 1997,vol. 9, pp. 694-701.
Moretta et al. Unravelling natural killer cell function: triggering; and inhibitory human NK receptors, "European Molecular Biology organisation", Year 2004, vol. 23, pp. 255-259.
Moretta et al., Activating Receptors and Coreceptors; Involved in Human Natural Killer; Cell-Mediated Cytolysis, "Annual Review of Immunology", Year 2001, vol. 19, pp. 197-223.
Ravetch et al.,Immune Inhibitory Receptors, "Science", Year 2000, vol. 290, pp. 84-89.
Sivori et al., CD94 functions as a natural killer cell inhibitory receptor for different HLA class I alleles: identification of the inhibitory form of CD94 by the use of novel monoclonal antibodies, "European journal of Immunology", Year 1996, vol. 26, pp. 2487-2492.
Van Beneden et al. Expression of Ly49E and CD94/NKG2 on Fetal and Adult NK Cells, "journal of Immunology", Year 2001, vol. 166, pp. 4302-4311.
Vance et al. Implications of CD94 deficiency and monoallelic; NKG2A expression for natural killer cell development and repertoire formation, "PNAS", Year 2002, vol. 99, pp. 868-873.
Vance et al. Recognition of the Class Ib Molecule Qa-Ib by Putative; Activating Receptors CD94/NKG2C and CD94/NKG2E on Mouse Natural Killer Cells; "Journal of Expieremental Medicine", Year 1999, vol. 190, No. 12, pp. 1801-1812.
Zambello et al., NK-type lymphoproliferative diseases of granular lymphocytes; Expression and function of KIR and natural cytotoxicity receptors in NK-type lymphoproliferative diseases of granular lymphocytes, "Blood", Year 2003, vol. 102, pp. 1797-1805.

(56) References Cited

OTHER PUBLICATIONS

Zhang et al.Natural killer cells trigger differentiation of monocytes in to dendritic cells, "Blood", Year 2007, vol. 110, No. 7, pp. 2484-2493.

* cited by examiner

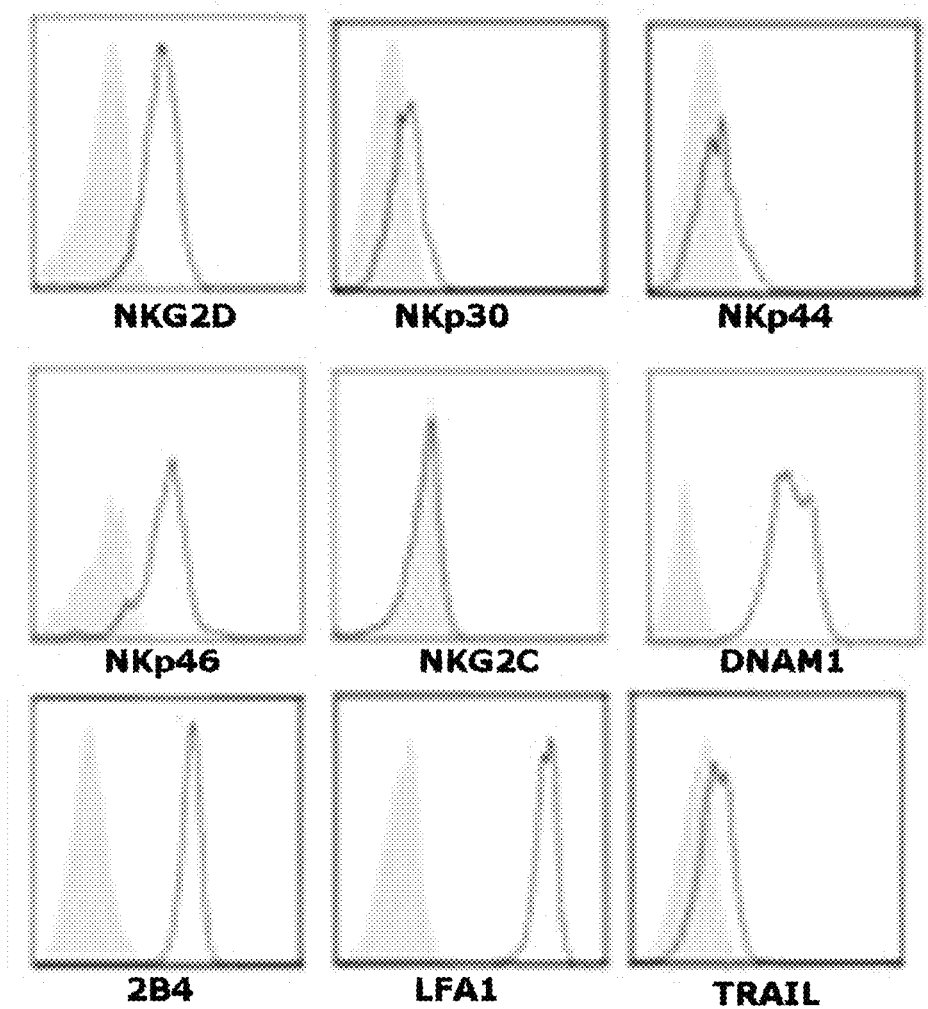
FIG. 3A(ii)

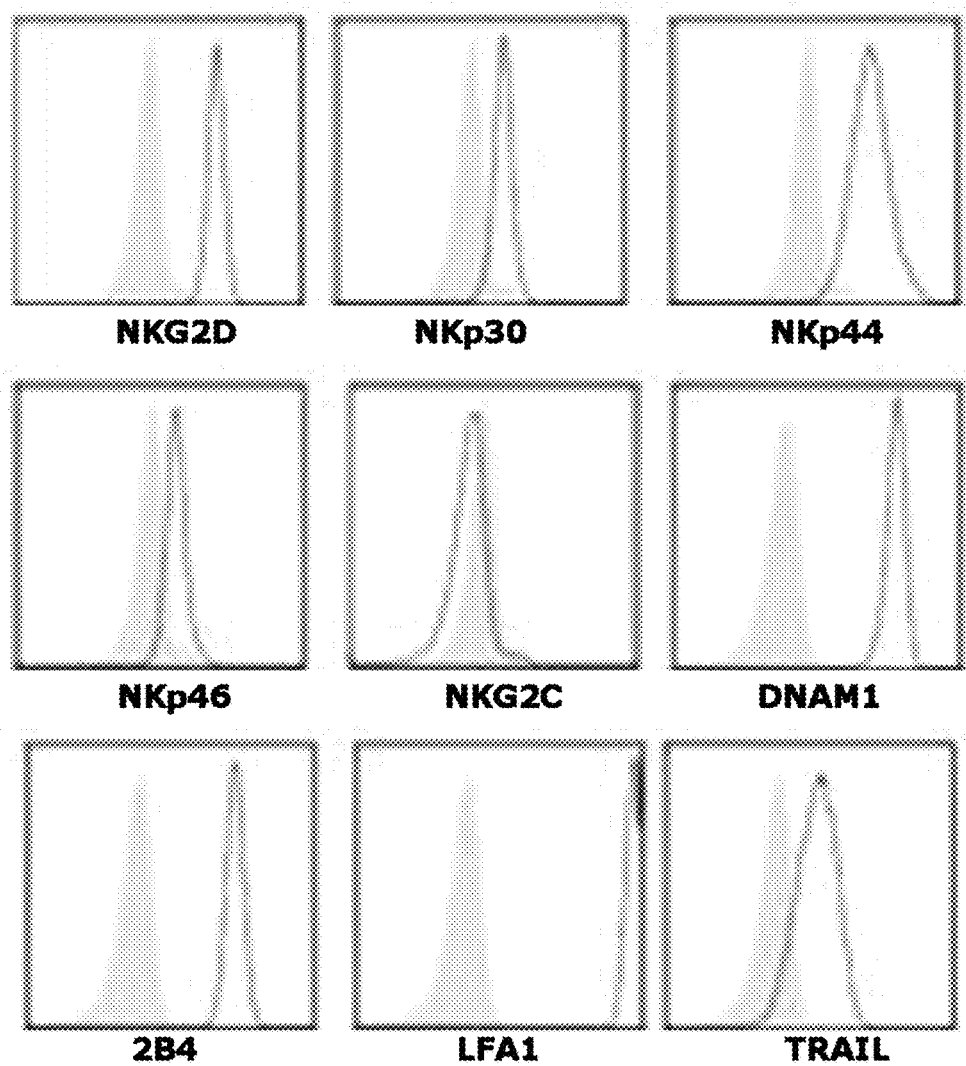
FIG. 3A.(iii)

FIG. 3B.(ii)

Donor ID:  1144-09      1591-08
FIG. 8A. 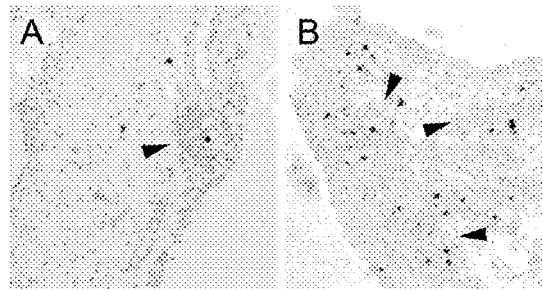 FIG. 8B.
NK cells
FIG. 8C. 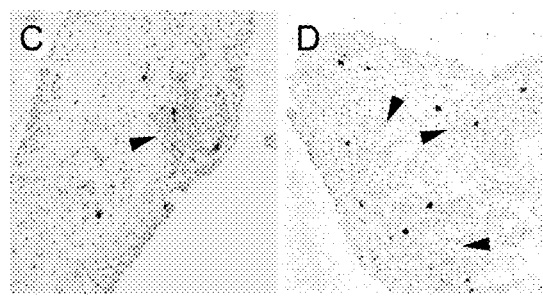 FIG. 8D.
NKG2A
FIG. 8E. 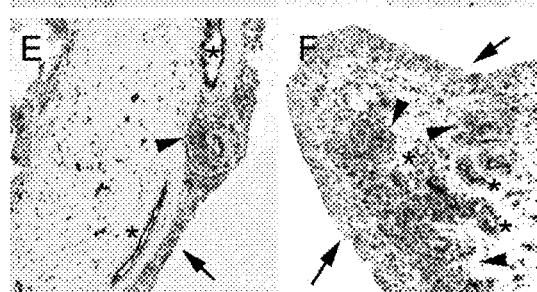 FIG. 8F.
HLA-E Donor ID: 1144-09        1591-08
FIG. 8G. 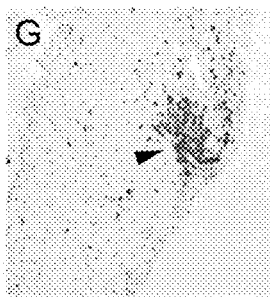 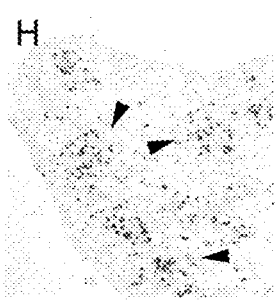 FIG. 8H.
T cells
FIG. 8I. 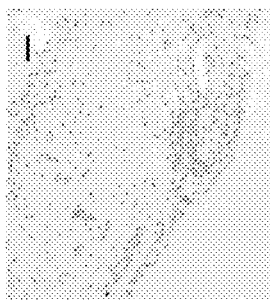 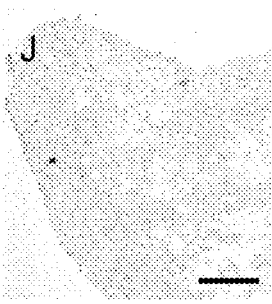 FIG. 8J.
Isotype
Donor ID: 1595-08
FIG. 8K. NK cells 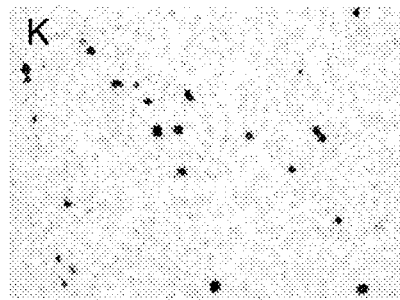
FIG. 8L. NKG2A⁺ cells 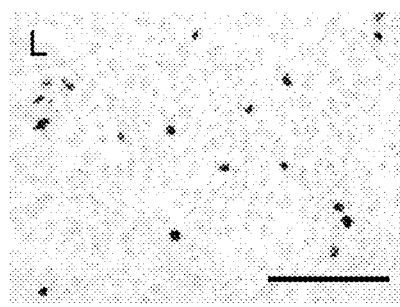

$r^2=0.136$
$p=0.3295$

FIG. 10A.
FIG. 10B.
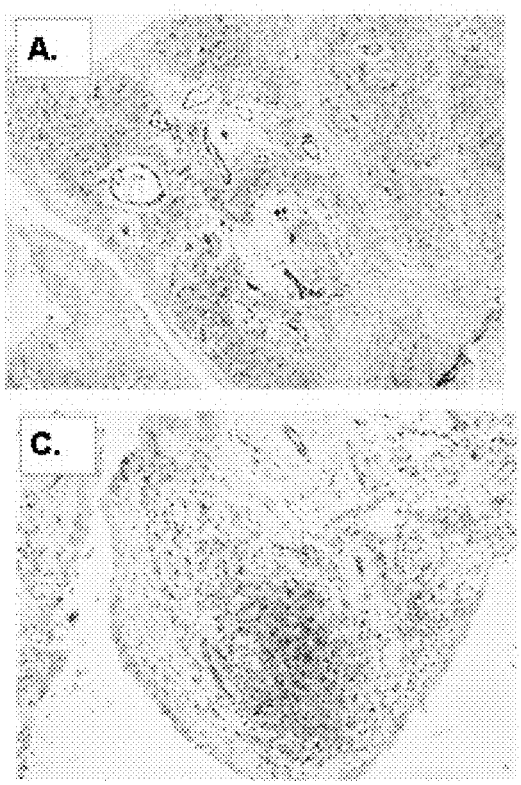
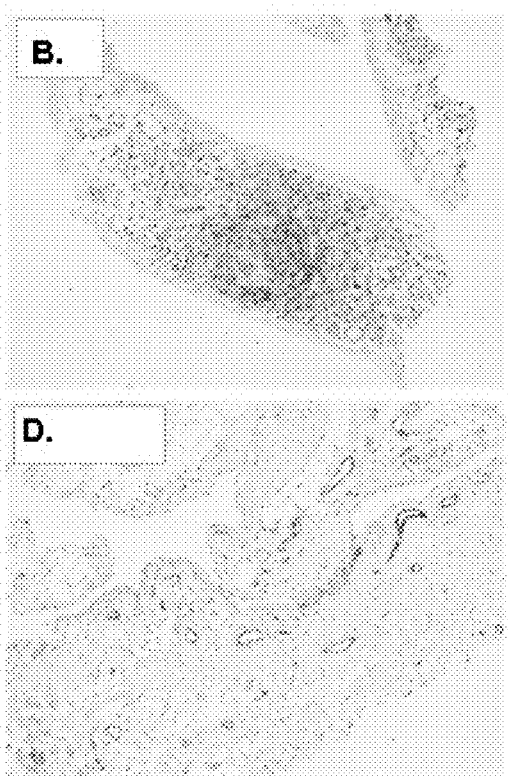
FIG. 10C.
FIG. 10D.

FIG. 11C.

SEQ. ID.NO. 3: humZ270 VL

DIQMTQSPSSLSASVGDRVTITCRASE NIYSYLAWYQQKPGKAPKLLI
NAKTLAEGVPS RFSGSGSGTDFTLTISSLQPEDFATYYCQHHYGTP
RTFGGGTKVEIK

FIG. 11D.

SEQ. ID. NO. 4: humZ199 VH

EVQLVESGGGLVKPGGSLRLSCAASGFTFSSYAMS WVRQAPGKGLEWVSEISS
GGSYTYYA DSVKGRFTISRDNAKNSLYLQMNSLRAEDTAVYYCARHGDYPRFF
DVWGQGTTVTVSS

FIG. 11E.

SEQ. ID. NO. 5: humZ199 VL

EIVLTQSPATLSLSPGERATLSCSASS SVSSYIYWYQQKPGQAPRLLIYLT
NLASGIPA RFSGSGSGTDFTLTISSLEPEDFAVYYCQQWSGNP YTFGQGTKLEIK

FIG. 11A.

SEQ. ID. NO. 1.: Human NKG2A

MDNQGVIYSDLNLPPNPKRQQRKPKGNKSSILATEQE-
ITYAELNLQKASQDFQGNDKTYHCKDLPSAPEKLIVGILGIICLILMASVVTIVVIP-
STLIQRHNNSSLNTRTQKARHCGHCPEEWITYSNSCY-
YIGKERRTWEESLLACTSKNSSLLSIDNEEEMKFLSIISPSS-
WIGVFRNSSHHPWVTMNGLAFKHEIKDSDNAELNCAVLQVNRLKSAQCGSSII
HCKHKL

FIG. 11B.

SEQ ID NO 2: humZ270 VH

QVQLVQSGAEVKKPGASVKVSCKASGYTFTSYWMN WVRQA
GQGLEWMGRIDP YDSETHYA QKLQGRVTMTTDTSTSTA
MELRSLRSDDTAVYYCARGG YDFDVGTLYWFF DVWGQGTTVTVS

```
                       SEQUENCE LISTING

<160> NUMBER OF SEQ ID NOS: 5

<210> SEQ ID NO 1
<211> LENGTH: 233
<212> TYPE: PRT
<213> ORGANISM: Homo sapiens

<400> SEQUENCE: 1

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225                 230
```

```
<210> SEQ ID NO 2
<211> LENGTH: 124
<212> TYPE: PRT
<213> ORGANISM: Artificial
<220> FEATURE:
<223> OTHER INFORMATION: humanized sequence

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120

<210> SEQ ID NO 3
<211> LENGTH: 107
<212> TYPE: PRT
<213> ORGANISM: Artificial
<220> FEATURE:
<223> OTHER INFORMATION: Humanized sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105

<210> SEQ ID NO 4
<211> LENGTH: 119
<212> TYPE: PRT
<213> ORGANISM: Artificial
<220> FEATURE:
<223> OTHER INFORMATION: Humanized sequence

<400> SEQUENCE: 4

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Glu Ile Ser Ser Gly Gly Ser Tyr Thr Tyr Tyr Ala Asp Ser Val
        50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                85                  90                  95

Ala Arg His Gly Asp Tyr Pro Arg Phe Phe Asp Val Trp Gly Gln Gly
            100                 105                 110

Thr Thr Val Thr Val Ser Ser
            115

<210> SEQ ID NO 5
<211> LENGTH: 107
<212> TYPE: PRT
<213> ORGANISM: Artificial
<220> FEATURE:
<223> OTHER INFORMATION: Humanized sequence

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Tyr
            20                  25                  30

Ile Tyr Trp Tyr Gln Gln Lys Pro Gly Gln Ala Pro Arg Leu Leu Ile
        35                  40                  45

Tyr Leu Thr Ser Asn Leu Ala Ser Gly Ile Pro Ala Arg Phe Ser Gly
        50                  55                  60

Ser Gly Ser Gly Thr Asp Phe Thr Leu Thr Ile Ser Ser Leu Glu Pro
65                      70                  75                  80

Glu Asp Phe Ala Val Tyr Tyr Cys Gln Gln Trp Ser Gly Asn Pro Tyr
                85                  90                  95

Thr Phe Gly Gln Gly Thr Lys Leu Glu Ile Lys
            100                 105
```

SELECTIVE ELIMINATION OF EROSIVE CELLS

CROSS-REFERENCE TO RELATED APPLICATIONS

This application is a 35 U.S.C. §371 National Stage application of International Application PCT/EP2012/061583 (WO 2012/172102 A1), filed Jun. 18, 2012, which claimed priority of European Patent Application 11170402.9, filed Jun. 17, 2011; this application claims priority under 35 U.S.C. §119 of U.S. Provisional Application 61/501,533; filed Jun. 27, 2011.

TECHNICAL FIELD

The present invention relates to treatment of bone erosion and cartilage destruction, in particular treatment of bone and cartilage destroying diseases using biological drugs such as antibodies.

In accordance with 37 C.F.R. §1.52(e)(5), Applicants enclose herewith the Sequence Listing for the above-captioned application entitled "SEQUENCE LISTING", created on Dec. 5, 2013. The Sequence Listing is made up of 7 kilobytes, and the information contained in the attached "SEQUENCE LISTING" is identical to the information in the specification as originally filed. No new matter is added.

BACKGROUND

Natural killer (NK) cells are bone marrow derived lymphocytes essential for host defense against certain infections and tumors. Upon activation they rapidly produce a range of cytokines and can mediate cytotoxic responses against infected, stressed, or tumorigenic cells. The role of NK cells in chronic inflammatory diseases is emerging, and it is becoming increasingly appreciated that NK cells may play an important role in the modulation of T and B cell responses through their capacity to promote differentiation and maturation of dendritic cells (DC) and subsequent polarization of T cell responses (see, e.g., Cooper et al. (2004) Trends Immunol. 25: 47-52; Zhang et al. (2007) Blood Oct 1; 110(7):2484-93). Furthermore, studies have shown that NK cells have the capacity to directly eliminate subsets of activated T cells via cell-mediated cytotoxic responses (Lu et al. (2007) Immunity. 26: 593-604). NK cell activity is regulated by a complex mechanism that involves both activating and inhibitory signals (see, e.g., Moretta et al. (2001) Annu Rev Immunol 19:197-223; Moretta et al. (2003) EMBO J EPub Dec 18; Ravetch et al. (2000) Science 290:84-89; Zambello et al. (2003) Blood 102:1797-805; Moretta et al. (1997) Curr Opin Immunol 9:694-701.

Several different NK-specific receptors have been identified that are involved in NK cell mediated recognition and killing of HLA Class I deficient target cells. One import inhibitory NK cell receptor is CD94/NKG2A, which interacts with the non-classical MHC class I molecule HLA-E (see, e.g., Braud et al. (1998) Nature 391:795-799; Lee et al. (1998) PNAS 95:5199-5204; Vance et al. (2002) PNAS 99:868-873; Brooks et al. (199) J Immunol 162:305-313; Miller et al. (2003) J Immunol 171:1369-75; Brooks et al. (1997) J Exp Med 185:795-800; Van Beneden et al. (2001) 4302-4311; US Patent application no. 20030095965).

CD94/NKG2A is an inhibitory receptor found on subsets of NK, NKT and T cells, which restricts their killing of cells expressing the CD94/NKG2A-ligand HLA-E carrying small peptides typically derived from the leader sequence of other MHC class I molecules (see, e.g., WO99/28748 and Braud et al. (1998) Nature 391:795-799).

Various antibodies against NKG2A have been described in the art. For example Sivori et al. (Eur J Immunol 1996; 26:2487) refers to the murine anti-NKG2A antibody Z270; Carretero et al. (J Exp Med 1999; 190:1801-12) refers to rat anti-murine NKG2A antibody 20D5; US patent application 20030095965 describes murine antibody 3S9, witch binds to NKG2A, NKG2C and NKG2E; patent application WO06070286 discloses monoclonal antibodies against NKG2A; and patent application WO2008/009545 describes the humanized antibody humZ270 and other anti-NKG2A antibodies with substantially identical variable heavy chain and/or variable light chain to those of Z270.

SUMMARY

Rheumatoid arthritis (RA) is a chronic inflammatory disease where activation of inflammatory mediators produced by multiple cellular subsets eventually results in destruction of joint cartilage and bone. It is generally accepted that the main cellular subsets responsible for cartilage and bone destruction in RA are fibroblast-like synoviocytes (FLS) and osteoclasts, respectively. CD94-NKG2A expressing T cells and NK cells can suppress inflammation by killing activated proinflammatory cells. Activation of these cells can be accomplished by a series of different cells and molecules including macrophages, activated CD4+ T cells and B cells/plasma cells. However, this regulatory, anti-inflammatory activity is inhibited when CD94-NKG2A receptors engage their HLA-E ligand at the surface of pro-inflammatory cells. By blocking CD94-NKG2A receptors and preventing their inhibitory signalling, NNC141-0100 enhances anti-inflammatory activities of regulatory CD94-NKG2A+ T cells and NK cells, boosting their ability to eliminate e.g. activated pro-inflammatory CD4+ T cells and fibroblast-like synoviocytes (FLS). A therapy that specifically eliminates aggressive cartilage-eroding FLS and suppresses the formation of bone erosive osteoclasts while leaving resting cells unaffected may have a significant advantage over current RA therapies and could potentially also, with benefit for the patients, be used in treating osteoarthritis (OA) and psoriatic arthritis (PsA)

This invention discloses how an anti-NKG2A antibody attenuates two major pathogenic pathways in RA, i.e. bone and cartilage erosion, by its capacity to reduce formation of bone-degrading osteoclasts and by selectively enhancing elimination of cartilage-degrading FLS, respectively.

Existing therapeutics targeting RA act directly on individual components of the inflammatory cascade, and their efficacy with regard to bone erosion is secondary to their anti-inflammatory effect. Anti-NKG2A mAbs capable of inhibiting binding of HLA-E or which can non-competitively block the function of CD94/NKG2A and stimulate the endogenous immune-regulatory mechanism of NK cells result in selective elimination of cells that promote degradation, bone erosion and reduction in IL-6, a cytokine known to promote inflammation. Thus, therapeutic treatment with an anti-NKG2A mAb can have a direct effect on the pathogenesis in diseases characterized by bone erosion or cartilage destruction.

The present invention discloses the use of an anti-NKG2A antibody, or a fragment thereof, capable of treating cartilage destruction and/or bone erosion.

The present invention discloses the use of an anti-NKG2A antibody for the treatment of a disease or disorder characterized by cartilage destruction and/or bone erosion.

The present invention discloses the use of an anti-NKG2A antibody for the treatment of cartilage destruction and/or bone erosion wherein the anti-NKG2A antibody stimulates selective elimination of activated cells that promote cartilage degradation or bone erosion. In one embodiment of the current invention the cartilage-degrading cells are fibroblast-like synoviocytes (FLS). In one embodiment the bone-eroding cells are erosive osteoclasts.

The present invention discloses the use of an anti-NKG2A antibody for the treatment of a disease or disorder characterized by cartilage destruction and/or bone erosion, wherein the anti-NKG2A antibody stimulates selective elimination of activated cells that promote cartilage degradation or bone erosion. In one embodiment of the current invention the cartilage-degrading cells are fibroblast-like synoviocytes (FLS). In one embodiment the bone-eroding cells are erosive osteoclasts.

The NKG2A antibodies used in the current invention can be any suitable anti NKG2A anti-NKG2A antibodies. In one embodiment, the antibody is a monoclonal anti-NKG2A antibody. In one embodiment, the antibody is a humanized anti-NKG2A antibody. In one embodiment, the antibody is a fully human anti-NKG2A antibody. In one embodiment, the antibody is an anti-NKG2A antibody as described in WO2008/009545. In one embodiment, the anti-NKG2A monoclonal antibody is humZ270 as described in patent publication WO2008/009545. In one embodiment, the anti-NKG2A antibody is a monoclonal anti-NKG2A antibody as described in patent publication WO09092805. In one embodiment, the anti-NKG2A antibody is humZ199 as described in patent publication WO09092805.

BRIEF DESCRIPTION OF DRAWINGS

[1] If relevant

FIG. 1 Illustrates the expression profile of a panel of cell surface molecules expressed by in vitro generated fibroblast-like synoviocytes derived from the synovial tissue of patients with rheumatoid arthritis (RA).

FIG. 2 shows that NKG2A expressing NK cells are present in RA synovium and can be found in areas containing HLA-E expressing RA-FLS.

FIG. 3. shows that NK cells, including synovial NK cells derived from RA patients, express a panel of activating receptors known to bind to ligands that are expressed on RA FLS RA-FLS.

FIG. 3A. (ii) shows resting CD56bright NK cells from PBMC derived from a representative healthy donor. CD56bright NK cells express NKG2D, NKp30, NKp44. NKp46, DNAM1, 2B4, LFA-1, and TRAIL, but no, or very low levels of NKG2C as indicated by the open histogram overlays.

FIG. 3A. (iii) shows Nishi NK cells. Nishi NK cells express NKG2D, NKp30, NKp44, NKp46, DNAM1, 2B4, LFA-1, and TRAIL, but no, or very low levels of NKG2C as indicated by the open histogram overlays.

FIG. 3B. (i) shows that NK cells co-cultured with RA-FLS overnight results in the elimination of adherent RA-FLS in a dose dependent manner.

FIG. 3B (ii). shows the well area covered by adherent RA-FLS when cultured alone, or when co-cultured with decreasing amounts of NK cells overnight, as analyzed by Immunospot image analysis.

FIG. 4. shows that RA-FLS are protected from NK cell-mediated cytotoxicity by expression of HLA-E capable of ligating to inhibitory CD94-NKG2A NK cell receptors.

FIG. 6. shows that NNC141-0100 (humZ270) inhibits formation of TRAP+ multinucleated osteoclasts:

FIG. 7:

Figure 1A:
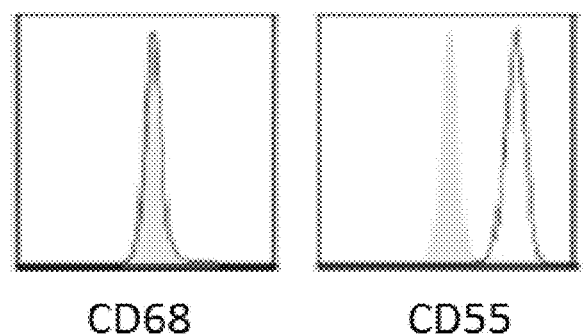
FIG. 1A. shows that fibroblast-like synoviocytes (FLS) derived from RA patients express CD55 (right histogram overlay) but lack CD68 (left histogram overlay).

8A. shows RA synovial tissue from ID 1144-09 stained for NK cells with an anti-NKp46 antibody.

8B. shows RA synovial tissue from ID 1591-08 stained for NK cells with an anti-NKp46 antibody.

8C. shows RA synovial tissue from ID 1144-09, stained for NKG2A with the Z199 antibody (an anti-NKG2A antibody).

8D. shows RA synovial tissue from ID 1591-08, stained for NKG2A with the Z199 antibody (an anti-NKG2A antibody).

8E. shows RA synovial tissue from ID 1144-09, stained for HLA-E with the 3D12 antibody.

8F. shows RA synovial tissue from ID 1591-08, stained for HLA-E with the 3D12 antibody.

8G. shows RA synovial tissue from ID 1144-09, stained for T cells with an anti-CD3 antibody.

8H. shows RA synovial tissue from ID 1591-08, stained for T cells with an anti-CD3 antibody.

8I. shows RA synovial tissue from ID 1144-09, stained with an IgG2b isotype control antibody.

8J. shows RA synovial tissue from ID 1591-08, stained with an IgG2b isotype control antibody.

8K. shows a high magnification picture of NKp46+ NK cells from ID 1595-08.

8L. shows a high magnification picture of NKG2A+ cells from ID 1595-08.

8M. shows a digital image analysis for correlation of the number of NKG2A+ cells in synovium from 15 RA patients with the number of NKp46+ NK cells.

FIG. 9. shows that NKG2A and its ligand, HLA-E, are expressed in synovium of patients with osteoarthritis (OA).

9A. depicts NKG2A+ cells (Z199 antibody) among infiltrating lymphocytes.

9B. depicts HLA-E expression (3D12 antibody) by infiltrating immune cells, endothelial cells and synoviocytes.

9C. shows a digital image analysis for correlation of the frequency of NKG2A+ cells with that of NK cells in OA synovium.

FIG. 10. shows that the CD94-NKG2A ligand was found to be expressed in inflamed synovium from not only RA and OA patients, but also PsA patients 10A. depicts staining of synovial tissue samples from RA patient.

10B. depicts staining of synovial tissue samples from PsA patient.

10C. depicts staining of synovial tissue samples from RO (OA????) patient.

10D. depicts staining of synovial tissue samples from normal control.

FIG. 11 shows the amino acid sequence of:

11A.: SEQ. ID. NO. 1, humNKG2A.

11B.: SEQ. ID. NO. 2, heavy chain variable domain (VH) of the humZ270 antibody.

11C.: SEQ. ID. NO. 3, light chain variable domain (VL) of the humZ270 antibody.

11D.; SEQ. ID. NO. 4, heavy chain variable domain (VH) of the humZ199 antibody.

11E. SEQ. ID. NO. 5, light chain variable domain (VL) of the humZ199 antibody.

DESCRIPTION

The term "antibody" as referred to herein refers to a polypeptide derived from a germline immunoglobulin sequence. The term includes full-length antibodies and any antigen binding fragments or single chains thereof. The terms "antibody", "monoclonal antibody" and "mAb", as used herein, are intended to refer to immunoglobulin molecules and fragments thereof that have the ability to specifically bind to an antigen. A sub-class of the immunoglobulins of particular pharmaceutical interest are those belonging to the IgG family, which can be subdivided into the iso-types IgG1, IgG2, IgG3 and IgG4. IgG molecules are composed of two heavy chains interlinked by two or several disulfide bonds and two light chains, one attached to each of the heavy chains by a disulfide bond. The IgG heavy chain is composed of four Ig-domains, including the variable domain (VII) and three constant domains (CH1, CH2, and CH3). Each light chain is comprised of a light chain variable region (VL) and a light chain constant region (CL). The variable regions of the heavy and light chains contain a binding domain that interacts with an antigen. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The constant regions of the antibodies may mediate the binding of the antibody to host tissues or factors, including various cells of the immune system (e.g., effector cells), Fc receptors (FcRs) and the first component (C1q) of the classical complement system. Binding to FcRs and C1q may mediate effects such as ADCC or CDC.

An antibody of the invention may be any NKG2A binding antibody, the humZ270 antibody (SEQ. ID. NO. 2 and SEQ. ID. NO. 3) or the humZ199 antibody (SEQ. ID. NO. 4 and SEQ. ID. NO. 5) or any other antibody of the invention, or a variant of any one of these antibodies.

The term humanized Z270 or humZ270 or hZ270, as used herein, comprises the antibody disclosed in the patent application WO08009545, which is hereby incorporated by reference into this application. The term humanized Z199 or humZ199 as used herein, comprises the antibody disclosed in the patent publication WO09092805, which is hereby incorporated by reference into this application.

As used herein, the term Ab comprises an antibody, or a fragment thereof, which specifically binds its corresponding Ag. Examples of antigen-binding fragments include, but are not restricted to, Fab, Fab', F(ab)2, F(ab')2, Fv (typically the VL and VH domains of a single arm of an antibody), single-chain Fv (scFv; see, e.g., Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., Protein Eng 1997; 10:949-57); camel IgG; IgNAR; and one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219; and published U.S. Patent Applications 20050238646 and 20020161201.

The term "antigen-binding fragment" of an antibody refers to one or more fragments of an antibody that retain the ability to specifically bind to an antigen, such as NKG2A or another target molecule as described herein. It has been shown that the antigen-binding function of an antibody can be performed by fragments of a full-length antibody. Examples of binding fragments encompassed within the term "antigen-binding fragment" of an antibody include a Fab fragment, a F(ab')2 fragment, a Fab' fragment, a Fd fragment, a Fv fragment, a ScFv fragment, a dAb fragment and an isolated complementarity determining region (CDR). Single chain antibodies such as scFv and heavy chain antibodies such as VHH and single domain camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

A "Fab" fragment includes a variable domain and a constant domain of the light chain and a variable domain and the first constant domain (CH1) of the heavy chain. A Fab' fragment includes one or more cysteine carboxy terminal linkages to the heavy or light chains. F(ab')2 antibody fragments comprise a pair of Fab fragments that are generally covalently linked near their carboxy termini by hinge cysteines. Other chemical couplings of antibody fragments are also known in the art. A Fab fragment retains the ability of the parent antibody to bind to its antigen, potentially with a lower affinity. F(ab')2 fragments are capable of divalent binding, whereas Fab fragments can bind monovalently only. Generally, Fab fragments lack the constant CH2 and CH3 domains, i.e. the Fc part, where interaction with the Fc receptors would occur. Thus, Fab fragments are in general devoid of effector functions.

An "Fv" fragment is an antibody fragment that contains a complete antigen recognition and binding site, and generally comprises a dimer of one heavy and one light chain variable domain in tight association that can be covalent in nature, for example in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen binding specificity to the antibody. However, even a single variable domain comprising only three hypervariable regions specific for an antigen has the ability to recognize and bind the antigen, although usually at a lower affinity than the entire binding site (Cai & Garen, Proc. Natl. Acad. Sci. USA, 93: 6280-6285, 1996). For example, naturally occurring camelid antibodies that only have a heavy chain variable domain (VHH) can bind antigens (Desmyter et al., J. Biol. Chem., 277: 23645-23650, 2002; Bond et al., J. Mol. Biol. 2003; 332: 643-655).

"Single-chain Fv" or "scFv" antibody fragments comprise the VH and VL domains of the antibody, where these domains are present in a single polypeptide chain. Generally, the Fv polypeptide further comprises a polypeptide linker between the VH and VL domains that enables the scFv to form the desired structure for antigen binding. For a review of scFv, see Pluckthun, 1994, in The Pharmacology of Monoclonal Antibodies, Vol. 113, Rosenburg and Moore eds. Springer-Verlag, New York, pp. 269-315.

The term "diabodies" refers to small antibody fragments with two antigen-binding sites, in which fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, Proc. Natl. Acad. Sci. USA, 90:6444-6448.

The expression "linear antibodies" refers to antibodies as described in Zapata et al., 1995, Protein Eng., 8(10):1057-1062. Briefly, these antibodies contain a pair of tandem Fd segments (VH-CH1-VH-CH1) that, together with complementary light chain polypeptides, form a pair of antigen binding regions. Linear antibodies can be bispecific or monospecific.

The term "monobody". as used herein, refers to an antigen-binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen-binding molecules connected by a disulfide bond. The heavy chain variable domain comprises one or more hypervariable regions, preferably a CDRH3 or HVL-H3 region.

The terms "hypervariable region", when used herein, refers to the amino acid residues of an antibody that are responsible for antigen binding. The hypervariable region comprises amino acid residues from a "complementarity-determining region" or "CDR" (defined by sequence as residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (defined by structure and differing for each antibody; see, for example, Chothia and Lesk, 1987, J. Mol. Biol. 196:901-917). In one example, HVL residues can include 26-32 (L1), 50-52 (L2) and 91-96 (L3) in the light chain variable domain and 26-32 (H1), 53-55 (H2) and 96-101 (H3) in the heavy chain variable domain.

Antibody fragments may be obtained using conventional recombinant or protein engineering techniques, and the fragments can be screened for binding to NKG2A, or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of any anti-NKG2A antibody, the humZ270 antibody (SEQ. ID. NO. 2 and SEQ. ID. NO. 3) or the humZ199 antibody (SEQ. ID. NO. 4 and SEQ. ID. NO. 5) or any other antibody of the invention, or a variant of any one of these antibodies. An antibody of the invention may be, or may comprise, an antigen binding portion of one of these antibodies, or variants thereof. For example, the antibody of the invention may be a Fab fragment of one of these antibodies or variants thereof, or it may be a single chain antibody derived from one of these antibodies, or a variant thereof.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). On the other hand, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivatives" refers to any modified form of the human antibody, such as a conjugate of the antibody and another agent or antibody.

The term "humanized antibody", as used herein, refers to a human/non-human chimeric antibody that contains a minimal sequence (CDR regions) derived from a non-human immunoglobulin. A humanized antibody is, thus, a human immunoglobulin (recipient antibody) in which residues from a hyper-variable region of the recipient are replaced by residues from a hypervariable region of a non-human species (donor antibody) such as from a mouse, rat, rabbit, or non-human primate, which have the desired specificity, affinity, and capacity. In some instances, FR residues of the human immunoglobulin are replaced by corresponding non-human residues. An example of such a modification is the introduction of one or more so-called back-mutations.

Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant segments.

The fragment crystallisable region ("Fc region"/"Fc domain") of an antibody is the "tail" region of an antibody comprising the constant CH2 and CH3 domains. The Fc domain may interact with cell surface receptors called Fc receptors, as well as some proteins of the complement system. The Fc region enables antibodies to activate the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody. Preferably, a modified Fc domain comprises one or more, preferably all of the following mutations that will result in decreased affinity to certain Fc receptors (L234A, L235E, and G237A) and in reduced C1q-mediated complement fixation (A330S and P331S), respectively.

The isotype of an antibody of the invention may be IgG, such as IgG1, IgG2, or IgG4. If desired, the class of an antibody may be "switched" by known techniques. For example, an antibody that was originally produced as an IgM molecule may be class switched to an IgG antibody. Class switching techniques may also be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

The term "epitope", as used herein, is defined in the context of a molecular interaction between an "antigen binding polypeptide", such as an antibody (Ab), and its corresponding "antigen" (Ag). The term antigen (Ag) refers to the molecular entity used for immunization of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process for raising the Ab.

Generally, "epitope" refers to the area or region on an Ag to which an Ab specifically binds, i.e. the area or region in physical contact with the Ab. A protein epitope may comprise amino acid residues in the Ag that are directly involved in binding to a Ab to an Ab (also called the immunodominant component of the epitope) and other amino acid residues, which are not directly involved in binding, such as amino acid residues of the Ag which are effectively blocked by the Ab (in other words, the amino acid residue is within the "solvent-excluded surface" and/or the "footprint" of the Ab). The term epitope herein includes both types of binding sites in any particular region of NKG2A that specifically binds to an anti-NKG2A antibody, or another NKG2A-specific agent according to the invention, unless otherwise stated (e.g., in some contexts the invention relates to antibodies that bind directly to particular amino acid residues). NKG2A may comprise a number of different epitopes, which may include, without limitation, (1) linear peptide epitopes, (2) conformational which consist of one or more non-contiguous amino acids located near each other in the mature NKG2A conformation; and (3) post-translational epitopes which consist, either in whole or part, of molecular structures covalently attached to NKG2A, such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair will be defined differently.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At an even less detailed level the epitope can be characterized by the amino acid residues that it comprises as defined by a specific criterion such as the distance between atoms in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as NKG2A residues characterized by having a heavy atom (i.e. a non-hydrogen atom) within a distance of 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residues are shared by the epitopes.

Epitopes characterized by competition binding are said to be overlapping if the binding of the corresponding Abs are mutually exclusive, i.e. binding of one Ab excludes simultaneous binding of the other Ab. The epitopes are said to be separate (unique) if the Ag is able to accommodate binding of both corresponding Abs simultaneously.

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in NKG2A.

The epitope and paratope for a given antibody (Ab)/antigen (Ag) pair may be identified by routine methods. For example, the general location of an epitope may be determined by assessing the ability of an antibody to bind to different fragments or variant NKG2A polypeptides. The specific amino acids within NKG2A that make contact with an antibody (epitope) and the specific amino acids in an antibody that make contact with NKG2A (paratope) may also be determined using routine methods. For example, the antibody and target molecule may be combined and the Ab/Ag complex may be crystallised. The crystal structure of the complex may be determined and used to identify specific sites of interaction between the antibody and its target.

Antibodies binding to the same antigen can be characterized with respect to their ability to bind to their common antigen simultaneously and may be subjected to "binning". In the present context the term "binning" refers to a method of grouping antibodies that bind to the same antigen. "Binning" of antibodies may be based on competition binding of two antibodies to their common antigen in assays based on standard techniques such as Surface Plasmon Resonance (SPR), ELISA or flow cytometry.

A "bin" is defined by a reference antibody. If a second antibody is unable to bind to the antigen at the same time as the reference antibody, the second antibody is said to belong to the same "bin" as the reference antibody. In this case the reference and the second antibody are competing for binding to the antigen, thus the pair of antibodies are termed "competing antibodies". If a second antibody is capable of binding to the antigen at the same time as the reference antibody, the second antibody is said to belong to a separate "bin". In this case the reference and the second antibody are not competing for binding to the antigen, thus the pair of antibodies is termed "non-competing antibodies".

Antibody "binning" does not provide direct information about the epitope. Competing antibodies, i.e. antibodies belonging to the same "bin", may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies have separate epitopes.

The term "binding affinity" is herein used as a measure of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to ka and $k_d$ through the equation $K_D = k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

Similarly, the specificity of an interaction may be assessed by determination and comparison of the $K_D$ value for the interaction of interest, such as a specific interaction between an antibody and an antigen, with the $K_D$ value of an interaction not of interest.

Typically, the $K_D$ for the antibody with respect to the target will be 2-fold, preferably 5-fold, more preferably 10-fold less than $K_D$ with respect to the other, non-target molecule such as unrelated material or accompanying material in the environment. More preferably, the $K_D$ will be 50-fold less, such as 100-fold less, or 200-fold less; even more preferably 500-fold less, such as 1,000-fold less, or 10,000-fold less.

The value of this dissociation constant can be determined directly by well-known methods, such as by standard assays to evaluate the binding ability of ligands such as antibodies towards targets, which are known in the art and include, for example, ELISAs, Western blots, RIAs, and flow cytometry analysis. The binding kinetics and binding affinity of the antibody can also be assessed by standard assays known in the art, such as SPR.

A competitive binding assay can be conducted in which the binding of the antibody to the target is compared to the binding of the target by another ligand of that target, such as another antibody.

An antibody of the invention may have a $K_D$ for its target of $1 \times 10^{-7}$M or less, $1 \times 10^{-8}$M or less, or $1 \times 10^{-9}$M or less, or $1 \times 10^{-10}$M or less, $1 \times 10^{-11}$M or less, or $1 \times 10^{-12}$M or less. The $K_D$ of an antibody of the current invention may be less than 0.8 nM, such as less than 0.7 nM, less than 0.6 nM, less than 0.5 nM, less than 0.4 nM, less than 0.3 nM, less than 0.2 nM, less than 0.1 nM, less than 0.05 nM, less than 0.025 nM, or less than 0.015 nM, such as between 0.015 nM and 0 nM.

The term "identity", as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci USA 89, 10915-10919 (1992) for the BLOSUM 62 comparison matrix) is also used by the algorithm.

Preferred parameters for a peptide sequence comparison include the following:

Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

The term "similarity" is a related concept, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% (fraction 15/20)). Therefore, in cases where there are conservative substitutions, the degree of similarity between two polypeptides will be higher than the percent identity between those two polypeptides.

A "receptor" is defined as a molecular structure present on the surface or inside of a cell. A receptor produces a characteristic cellular response, i.e. biological activity, when a ligand binds. A "ligand" for a receptor is defined as any molecule (e.g. peptide, polypeptide, carbohydrate, small molecule or ion) that selectively is capable of binding to the receptor. An agonistic ligand ("agonist") is a ligand that upon binding to the receptor to some degree is capable of eliciting the characteristic response for the receptor. An antagonistic ligand ("antagonist") is a ligand that has the ability to bind to the receptor and to some degree block the action of an agonist, e.g. the natural ligand of the receptor.

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/γ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. Human NKG2A comprises 233 amino acids in 3 domains, with a cytoplasmic domain comprising residues 1-70, a transmembrane region comprising residues 71-93, and an extracellular region comprising residues 94-233, of the following sequence:

```
                                               (SEQ ID NO: 1)
MDNQGVIYSDLNLPPNPKRQQRKPKGNKSSILATEQEITYAELNLQKAS

QDFQGNDKTYHCKDLPSAPEKLIVGILGIICLILMASVVTIVVIPSTLI

QRHNNSSLNTRTQKARHCGHCPEEWITYSNSCYYIGKERRTWEESLLAC

TSKNSSLLSIDNEEEMKFLSIISPSSWIGVFRNSSHHPWVTMNGLAFKH

EIKDSDNAELNCAVLQVNRLKSAQCGSSIIYHCKHKL.
```

HLA-E (OMIM 143010, the entire disclosure of which is herein incorporated by reference) is a nonclassical MHC molecule that is expressed on the cell surface and regulated by the binding of peptides derived from the signal sequence of other MHC class I molecules. HLA-E binds natural killer (NK) cells and some T cells, binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E is sufficient to protect target cells from lysis by CD94/NKG2A+NK, T, or NKT cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

In the context of the present invention, "an agent that binds to human CD94/NKG2A receptor" or "an anti-NKG2A antibody" or "NKG2A binding antibody" refers to an any agent and/or antibody with detectable binding to human CD94/NKG2A receptor using any standard assay where the agent and/or antibody is incubated in the presence of CD94/NKG2A or NKG2A and binding detected via, e.g., radiolabels, physical methods such as mass spectrometry, or direct or indirect fluorescent labels detected using, e.g., cytofluorometric analysis (e.g. FACScan). Any amount of binding above the amount seen with a control, non-specific agent indicates that the agent binds to the target.

The term humanized Z270 or humZ270 or hZ270, as used herein, comprises the antibody (SEQ. ID. NO. 2 and SEQ. ID. NO. 3) disclosed in the patent publication WO08009545, which is hereby incorporated by reference into this application. The term humanized Z199 or humZ199, as used herein, comprises the antibody (SEQ. ID. NO. 4. and SEQ. ID. NO. 5) disclosed in the patent publication WO09092805 which is hereby incorporated by reference into this application.

"Protractive groups"/"half-life extending moieties" are herein understood as one or more chemical groups attached to one or more amino acid site chain functionalities such as —SH, —OH, —COOH, —CONH2, —NH2, or one or more N- and/or O-glycan structures and that can increase in vivo circulatory half-life of therapeutic proteins/peptides when conjugated to these proteins/peptides. Examples of "protractive groups" include but are not limited to: Biocompatible fatty acids and derivatives thereof, Hydroxyalkyl Starch (HAS) e.g. Hydroxvethyl Starch (HES), Polyethylene Glycol (PEG), Poly (Glyx-Sery)n (HAP), Hyaluronic acid (HA), Heparosan polymers (IIEP), Phosphorylcholine-based polymers (PC polymer), Fleximers, Dextran, Polysialic acids (PSA), an Fc domain, Transferrin, Albumin, Elastin-like peptides, XTEN polymers, Albumin binding peptides, a CTP peptide, and any combination thereof.

The term "NKG2A Fc fusion protein" is herein meant to encompass NKG2A fused to an Fc domain that can be derived from any antibody isotype.

Inflammation is the complex biological response of tissues to a variety of stimuli, including pathogens, damaged cells, or irritants. Inflammation is a protective response by the organism to remove or isolate the injurious stimuli and initiate the healing process. Inflammation is not a synonym for infection—infection is invasion of an organism by an exogenous pathogen, while inflammation is the immune system's response to the pathogen.

Inflammation is a cascade of events involving multiple components, including the vasculature (e.g., endothelial cells, pericytes, smooth muscle cells), cells of the immune system (e.g., T and B lymphocytes, monocytes, dendritic cells, neutrophils), cell-derived soluble mediators (cytokines, chemokines) and also resident cells in the targeted tissue (e.g., epithelial cells, synovial fibroblasts, neuronal cells). Acute inflammation is of short duration (hours to days) and largely involves resident cells in tissue, migration of leukocytes and exudation of fluid and plasma proteins to site of inflammation. This results from changes in vascular flow, cell activation and cellular components that attract leukocytes from circulation into the site of injury. Chronic inflammation is of prolonged duration in which active inflammation, tissue destruction and attempt at repair proceed simultaneously. Chronic inflammation can result from persistent infection, prolonged and repeated exposure to toxic agents or autoimmunity, a phenomenon by which the body's immune cells attack their own tissues, causing damage.

Normally, the immune system is able to distinguish between the body's normal cells (or "self") and foreign pathogens or abnormal cells ("non-self"). In some instances, the immune system loses the ability to recognize "self" as normal and inappropriately initiates a response against tissue or cells. This response stems from a loss of tolerance to self and is termed "autoimmunity". The pathologies resulting from autoimmunity often have serious clinical consequences and are one of the major health problems in the world, especially in developed nations. Examples of such autoimmune diseases include rheumatoid arthritis (RA), psoriasis, psoriatic arthritis, systemic lupus erythematosus (SLE), lupus nephritis, type I diabetes, Graves' disease, inflammatory bowel disease (IBD), Crohn's disease (CD), ulcerative colitis (UC), irritable bowel syndrome, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft vs. host disease, Sjögren's syndrome, autoimmune nephritis, Goodpasture syndrome, chronic inflammatory demyelinating polyneuropathy, allergy, asthma and other autoimmune diseases that are a result of either acute or chronic inflammation.

The process by which the immune system loses the ability to recognize "self" as normal, and the subsequent response directed against the tissue or cells, results in loss of tolerance, a state of "autoimmunity". The pathologies resulting from autoimmunity often have serious clinical consequences and are one of the major health problems in the world.

Targeted biological therapeutics are now available for the treatment of certain autoimmune diseases and/or chronic inflammatory diseases. For example, patients with rheumatoid arthritis may be treated with anti-CD20, a TNF antagonist (soluble TNFR or anti-TNF-α); patients with psoriasis may be treated with anti-CD11a; patients with multiple sclerosis may be treated with INF-beta; patients with ulcerative colitis may be treated with anti-TNF-α; and patients with Crohn's disease may be treated with anti-TNF-α or anti-CD4 integrin. Unfortunately, a large number of patients that receive treatment with any one of these biologics can experience a variety of side effects, could fail to respond, and/or can develop neutralizing antibodies against the drug. There is still a need for alternative biological medicaments which specifically target pathologies, but which do not affect healthy cells/tissue, which result in fewer or less severe side effects, which may be used long-term and/or which do not result in the generation of neutralizing antibodies. The current invention relates to these unmet needs amongst patients with autoimmune and/or chronic inflammatory diseases, disclosing antibodies that are suitable for use in such treatment.

Rheumatoid arthritis (RA) is a systemic disease that affects the entire body and is one of the most common forms of arthritis. It is characterized by inflammation of the joints, which causes pain, stiffness, warmth, redness and swelling. This inflammation is a consequence of inflammatory cells invading the joints and releasing enzymes that may digest bone and cartilage. As a result this inflammation can lead to severe bone and cartilage damage and to joint deterioration and severe pain among other physiological effects. The involved joint can lose its shape and alignment, resulting in pain and loss of movement.

There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors.

Cartilage erosion or cartilage destruction associated with RA is mainly driven by subsets of Fibroblast-like synoviocytes (FLS) present in the synovial intimal lining. The FLS, sometimes also referred to as Type B synoviocytes or RA synovial fibroblasts (BASF), are of mesenchymal origin and play a key role by producing cytokines that perpetuate inflammation, and they are principal producers of proteases that contribute to cartilage destruction. In RS, FLS develop an aggressive phenotype capable of invading into the extracellular cartilage matrix and further exacerbating joint damage.

Cartilage erosion or cartilage destruction, as referred to in this application, is the loss or degradation of the cartilage tissue.

Cartilage erosion or cartilage destruction as referred to in this application, is the loss or degradation of the cartilage tissue.

Bone resorption, the removal of osseous tissue by osteoclasts, is the unique function of the osteoclasts, which are specialized multinucleated cells derived from the monocyte cell lineage. Their differentiation is regulated by macrophage colony-stimulating factor, RANK ligand, and osteoprotegerin as well as multiple other mediators that may either positively or negatively regulate their differentiation, activation, and/or survival. The osteoclast develops a specialized cytoskeleton that permits it to establish an isolated microenvironment between itself and bone, wherein degradation of bone protein and minerals occurs by a process involving proton transport and enzyme release.

Bone erosion, as referred to in this application, is the loss of bone mass or bone mineral density that happens when there is a slight (or more than slight) but persistent elevation in the rate of bone resorption over the rate of bone formation.

Osteoarthritis (OA) is the most prevalent type of arthritis, particularly in adults 65 years and older. The disease is characterized by chronic degenerative arthropathy that frequently leads to chronic pain and disability. The reported incidence and prevalence rates of OA in specific joints vary widely, due to differences in the case definition of OA. For example, OA may be defined by radiographic criteria alone (radiographic OA), by typical symptoms (symptomatic OA), or by both. Using radiographic criteria, the distal and proximal interphalangeal joints of the hand have been identified as the joints most commonly affected, but they are the least likely to be symptomatic. In contrast, the knee and hip, which constitute the second and third most common locations of radiographic OA, respectively, are nearly always symptomatic. The first metatarsal phalangeal and carpometacarpal joints are also frequent sites of radiographic OA, while the shoulder, elbow, wrist and metacarpophalangeal joints rarely develop idiopathic OA.

Age is the most consistently identified risk factor for OA and prevalence rates rise steeply after age 50 in men and age 40 in women. OA is diagnosed by a triad of typical symptoms, physical findings and radiographic changes. The American College of Rheumatology has set forth classification criteria to aid in the identification of patients with symptomatic OA that include, but do not rely solely on, radiographic findings. Patients with early disease experience localized joint pain that worsens with activity and is relieved by rest, while those with severe disease may have pain at rest. Weight bearing joints may "lock" or "give way" due to internal derangement that is a consequence of advanced disease. Stiffness in the morning or following inactivity ("gel phenomenon") rarely exceeds 30 minutes.

Physical findings in osteoarthritic joints include bony enlargement, crepitus, cool effusions, and decreased range of motion. Tenderness on palpation at the joint line and pain on passive motion are also common, although not unique to OA. Radiographic findings in OA (slide) include osteophyte formation, joint space narrowing, subchondral sclerosis and cysts. The presence of an osteophyte is the most specific radiographic marker for although it is indicative of relatively advanced disease.

Radiographs are considered the "gold standard" test for the diagnosis of OA, but radiographic changes are evident only relatively late in the disease. The need is great for a sensitive and specific biological marker that would enable early diagnosis of OA, and monitoring of its progression. Routine laboratory studies, such as sedimentation rates and c-reactive protein, are not useful as markers for OA, although a recent study suggests that elevation of CRP predicts more rapidly progressive disease. Several epitopes of cartilage components, however, have been described that offer some promise as markers of OA. For example, chondroitin sulfate epitope 846, normally expressed only in fetal and neonatal cartilage, has been observed in OA, but not normal adult, cartilage and synovial fluid. Along a similar vein, an epitope unique to type II collagen has been described in OA cartilage, and can be unmasked in vitro by exposing normal cartilage to MMPs. This epitope can be measured in blood and urine and may prove useful in diagnosing or monitoring OA progression. Elevated serum hyaluronan levels have also been shown by some to correlate with radiographic OA. The finding of elevated cartilage oligomeric protein (COMP) levels in synovial fluid after traumatic joint injury may portend development of OA in the injured joint. Other potential markers of OA are listed but are either not easily accessible or lack the sensitivity and specificity required to consider them as potential OA markers.

Clinical symptoms of inflammation, the presence of histological inflammation in OA synovial tissue and early cartilage lesions at the border of the inflamed synovium are strong indicators that synovitis is a pivotal factor in the pathogenesis of OA. The traditional view of OA as a cartilage only disease is obsolete. OA should now be considered to be a whole joint disease that includes the synovial tissue. Bone, cartilage and synovium communicate by way of cell-cell interactions, through the release of soluble mediators and via mechanical signals. Synovial inflammation, despite not being a prerequisite for the development of OA, is clearly involved in cartilage breakdown and thus in the progression of the disease. Targeting the inflammatory synovium should delay or prevent articular cartilage damage and the formation of osteophytes, especially in early OA.

Psoriatic arthritis is a type of inflammatory arthritis that occurs in a subset of patients with psoriasis. In these patients, the skin pathology/symptoms are accompanied by joint swelling, similar to that seen in rheumatoid arthritis. It features patchy, raised, red areas of skin inflammation with scaling. Psoriasis often affects the tips of the elbows and knees, the scalp, the navel, and around the genital areas or anus.

The term "psoriatic arthritis" denotes a heterogeneous group of arthritides ranging from peripheral monoarticular, oligoarticular and polyarticular disease, to axial skeletal involvement. Yet, despite this apparent clinical heterogeneity, these various presentations are unified in their occurrence in individuals with cutaneous manifestations of psoriasis, rheumatoid factor sero-negativity, similar human leukocyte antigen (HLA) associations and radiographic similarities.

Approximately 2% of the Caucasian population in North America has psoriasis. Of these, 5-7% are affected by an inflammatory arthritis in some form. Overall, men and women are affected with equal frequency, though the actual male:female ratio may vary depending upon the subset in question. The peak incidence is in the 4th through 6th decades. Psoriatic skin disease pre-dates the onset of arthritis in 70% of cases, presents coincident with arthritis in 15% of cases, and follows the onset of arthritis in 15% of cases.

The cause of psoriatic arthritis is unknown. Peripheral joint activity in psoriatic arthritis parallels cutaneous activity in $1/3$ of cases, whereas activity of the skin and axial skeletal disease are likely to be discordant. Genetic factors appear to play an important role. There is a 70% concordance for psoriasis in monozygotic twins. There is a 50-fold increased risk of developing psoriatic arthritis in first-degree relatives of patients with the disease. There is a 2-fold increased risk of disease "transmission" by an affected father as compared to an affected mother. There are epidemiologic associations with the expression of both class I and class II HLA alleles. Environmental factors have been implicated. Streptococcal infection can precipitate the development of guttate psoriasis. HIV infection can present with both psoriasis and psoriatic arthritis, as well as worsen existing disease. Physical trauma has been reported to precipitate the development of arthritis, suggesting that psoriatic arthritis is the manifestation of a "deep Koebner phenomenon". The inflammatory and autoimmune character of the disease is supported not only by the clinical presentation, but also by the role that T-cells and various cytokines have been demonstrated to play in both the initiation and perpetuation of disease activity.

Factors that may portend a worse prognosis include extensive skin involvement; a strong family history of psoriasis; female gender; disease onset at <20 years of age; expression of HLA-B27, -DR3 or -DR4 alleles; and polyarticular or erosive disease.

Osteoporosis (OP) is a disease of bones that leads to an impaired bone strength and increased risk of fracture (see e.g. Theill et al. (2002) Annu Rev Immunol 20:795-23). In osteoporosis the bone mineral density (BMD) is reduced and the bone microarchitecture is gradually deteriorating, As defined by the World Health Organization (WHO) the disease is defined by a bone mineral density that is 2.5 standard deviations or more below the mean peak bone mass (average of young, healthy adults). The disease may be classified as primary type 1, primary type 2, or secondary. The form of osteoporosis most common in women after menopause is referred to as primary type 1 or postmenopausal osteoporosis. Primary type 2 osteoporosis (or senile osteoporosis) occurs after age 75 and is seen in both females and males at a ratio of 2:1. Finally, secondary osteoporosis may arise at any age and affects men and women equally. This form of osteoporosis results from chronic predisposing medical problems or disease, or prolonged use of medications such as glucocorticoids. Bone resorption is a major pathological factor in postmenopausal osteoporosis. Rapid or relatively rapid loss of bone mass/bone mineral density is often caused by an increase in number of osteoclasts or by excessive osteoclast activity (Walsh et al. (2005) Immunol Rev 208: 228-251).

Osteoporosis risks can be reduced with lifestyle changes (e.g. diet, exercise, fall prevention) and sometimes medication (e.g. calcium, vitamin D, bisphosphonates and several others).

The term "treatment", as used herein, refers to the medical therapy of any human. Said subject is expected to have undergone physical examination by a medical practitioner, who has given a tentative or definitive diagnosis which would indicate that the use of said specific treatment is beneficial to the health of said human subject. The timing and purpose of said treatment may vary from one individual to another, according to the status quo of the subject's health. Thus, said treatment may be prophylactic, palliative, symptomatic and/or curative.

In terms of the present invention, prophylactic, palliative, symptomatic and/or curative treatments may represent separate aspects of the invention.

In one aspect, the present invention provides compositions and formulations comprising molecules of the invention, such as the antibodies, antigen binding fragments of antibodies, polynucleotides, vectors and cells described herein. For example, the invention provides a pharmaceutical composition that comprises one or more antibody or antigen binding fragment of antibodies of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise a buffer system, preservative(s), tonicity agent(s), chelating agent(s), stabilizers and surfactants. The use of preservatives, isotonic agents, chelating agents, stabilizers and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension. The terms "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

In the context of the present invention "selective elimination of cartilage destructive cells" refers to a process in which an antibody against NKG2A increases NK cell mediated elimination of cartilage destructive cells, such as fibroblast-like synoviocytes (FLS) or other cartilage destructive cells, while not increasing the elimination of normal fibroblasts, such as e.g. foreskin fibroblasts (FSK4 cells) or other normal fibroblast cells. This selective elimination can be measured for example by a standard LDH release assay or other known suitable assays, in which the capacity of the therapeutic compound to eliminate the cartilage destructive cells is measured (see Example 4 and FIG. 5B). In one embodiment, an anti-NKG2A antibody causes at least 5% increase in the specific cytotoxicity of the cartilage destructive cells, or at least 10% increase in the specific cytotoxicity of the cartilage destructive cells. In one embodiment, an anti-NKG2A antibody causes at least 20% increase in the specific cytotoxicity of the cartilage destructive cells, or at least 30% increase in the specific cytotoxicity of the cartilage destructive cells. In one embodiment, an anti-NKG2A antibody causes at least 40% increase in the specific cytotoxicity of the cartilage destructive cells, or at least 50% increase in the specific cytotoxicity of the cartilage destructive cells. In one embodiment, an anti-NKG2A antibody causes at least 60% increase in the specific cytotoxicity of the cartilage destructive cells, or at least 70% increase in the specific cytotoxicity of the cartilage destructive cells. In one embodiment, an anti-NKG2A antibody causes at least 80% increase in the specific cytotoxicity of the cartilage destructive cells, or at least 90% increase in the specific cytotoxicity of the cartilage destructive cells. In one embodiment, an anti-NKG2A antibody causes at least 100% increase in the specific cytotoxicity of the cartilage destructive cells, or at least 125% increase in the specific cytotoxicity of the cartilage destructive cells. In one embodiment, an anti-NKG2A antibody causes at least 150% increase in the specific cytotoxicity of the cartilage destructive cells, or at least 175% increase in the specific cytotoxicity of the cartilage destructive cells. In one embodiment, an anti-NKG2A antibody causes at least 200% increase in the specific cytotoxicity of the cartilage destructive cells, or at least 225% increase in the specific cytotoxicity of the cartilage destructive cells. In one embodiment, an anti-NKG2A antibody causes at least 250% increase in the specific cytotoxicity of the cartilage destructive cells, or at least 275% increase in the specific cytotoxicity of the cartilage destructive cells. In one embodiment, an anti-NKG2A antibody causes at least 300% increase in the specific cytotoxicity of the cartilage destructive cells, or at least 350% increase in the specific cytotoxicity of the cartilage destructive cells. In one embodiment, an anti-NKG2A antibody causes at least 400% increase in the specific cytotoxicity of the cartilage destructive cells, or at least 500% increase in the specific cytotoxicity of the cartilage destructive cells.

In the context of the present invention "reduces formation of bone eroding cells" refers to a process in which an anti-NKG2A antibody reduces the formation of bone eroding cells, such as osteoclasts, TRAP+ multinucleated cells or other bone eroding cells.

The reduced formation of bone eroding cells can be measured in vitro by visual counting of adherent bone eroding cells (see Example 6. and FIG. 6C.) or any other suitable method of measuring the reduced formation of the bone eroding cells. In one embodiment an anti-NKG2A antibody causes at least 5% reduction of bone eroding cells or at least 10% reduction of bone eroding cells. In one embodiment an anti-NKG2A antibody causes at least 20% reduction of bone eroding cells or at least 30% reduction of bone eroding cells. In one embodiment an anti-NKG2A antibody causes at least 40% reduction of bone eroding cells or at least 50% reduction of bone eroding cells. In one embodiment an anti-NKG2A antibody causes at least 60% reduction of bone eroding cells or at least 70% reduction of bone eroding cells. In one embodiment an anti-NKG2A antibody causes at least 80% reduction of bone eroding cells or at least 90% reduction of bone eroding cells. In one embodiment an anti-NKG2A antibody causes at least 100% reduction of bone eroding cells or at least 125% reduction of bone eroding cells. In one embodiment an anti-NKG2A antibody causes at least 150% reduction of bone eroding cells or at least 175% reduction of bone eroding cells. In one embodiment an anti-NKG2A antibody causes at least 200% reduction of bone eroding cells or at least 225% reduction of bone eroding cells. In one embodiment an anti-NKG2A antibody causes at least 250% reduction of bone eroding cells or at least 275% reduction of bone eroding cells. In one embodiment an anti-NKG2A antibody causes at least 300% reduction of bone eroding cells or at least 350% reduction of bone eroding cells. In one embodiment an anti-NKG2A antibody causes at least 400% reduction of bone eroding cells or at least 450% reduction of bone eroding cells. In one embodiment an anti-NKG2A antibody causes at least 500% reduction of bone eroding cells.

Furthermore "reduces formation of bone eroding cells" in the context of present invention refers to reduced bone mineral erosion in vitro.

The reduced in vitro bone mineral erosion can be measured by culturing the cells or tissue on bone mineral discs (i.e. osteologic discs) or by other suitable methods. (See Example 6. and FIGS. 6D, 6E, 6F and 6G). In one embodiment an anti-NKG2A causes a 10% reduction in bone mineral erosion or 20% reduction in bone mineral erosion. In one embodiment an anti-NKG2A causes a 30% reduction in bone mineral erosion or 40% reduction in bone mineral erosion. In one embodiment an anti-NKG2A causes a 50% reduction in bone mineral erosion or 60% reduction in bone mineral erosion. In one embodiment an anti-NKG2A causes a 70% reduction in bone mineral erosion or 80% reduction in bone mineral erosion. In one embodiment an anti-NKG2A causes a 90% reduction in bone mineral erosion or 100% reduction in bone mineral erosion. In one embodiment an anti-NKG2A causes a 125% reduction in bone mineral erosion or 150% reduction in bone mineral erosion. In one embodiment an anti-NKG2A causes a 175% reduction in bone mineral erosion or 200% reduction in bone mineral erosion. In one embodiment an anti-NKG2A causes a 250% reduction in bone mineral erosion or 300% reduction in bone mineral erosion. In one embodiment an anti-NKG2A causes a 350% reduction in bone mineral erosion or 400% reduction in bone mineral erosion. In one embodiment an anti-NKG2A causes a 450% reduction in bone mineral erosion or 500% reduction in bone mineral erosion. In one embodiment an anti-NKG2A causes a 550% reduction in bone mineral erosion or 600% reduction in bone mineral erosion. In one embodiment an anti-NKG2A causes a 650% reduction in bone mineral erosion or 700% reduction in bone mineral erosion.

EXAMPLES

Example 1

Cell Surface Molecules Expressed on Fibroblast-Like Synoviocytes from RA Patients In FIG. 1A. adherent RA-FLS derived from RA synovial tissue were detached using 2 mM EDTA and surface stained for expression of fibroblast-marker CD55 (open histogram; right panel) and macrophage-marker CD68 (open histogram; left panel). The gray histogram represents the staining using an isotype control antibody. As seen in FIG. 1A, the RA-FLS show homogenous expression of CD55 and lack of CD68 confirms the fibroblast-like origin of adherent RA-FLS.

Figure 1B:
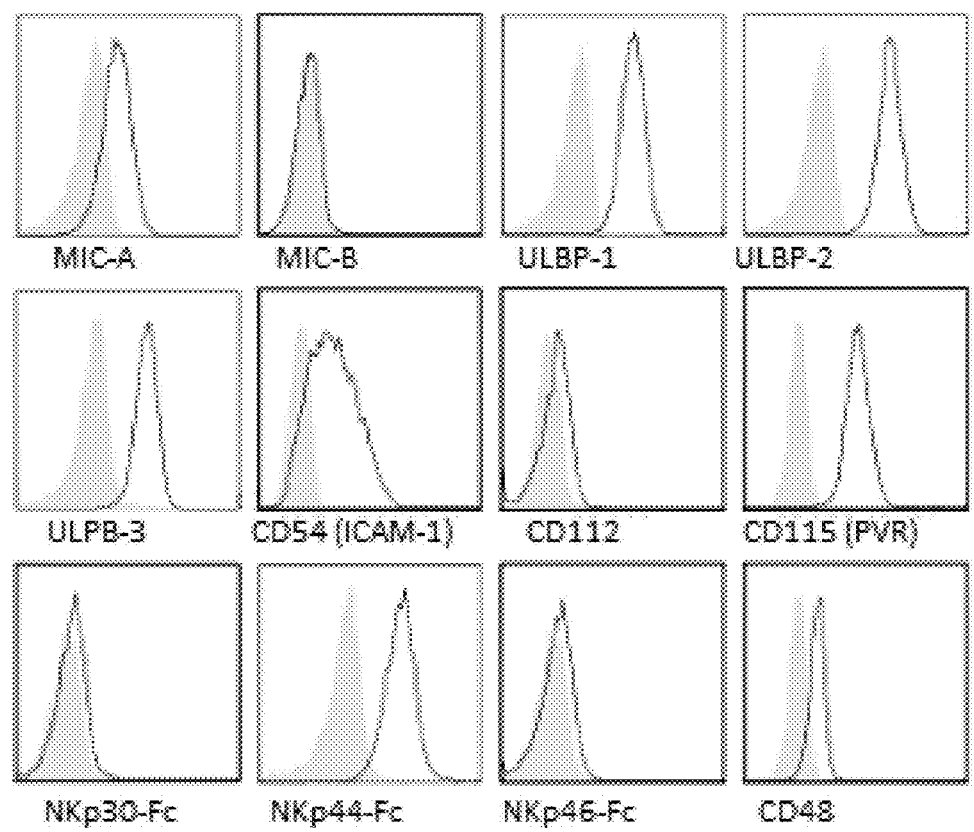
FIG. 1B. shows that RA-FLS cell surfaces express several ligands for activating NK cell receptors (e.g. MICA, ULBP1, ULBP2, ULBP3, ICAM1, CD155, CD48) as indicated below each histogram overlay. As indicated RA-FLS stain effectively with NKp44-FC fusion suggesting that RA-FLS express a putative ligand for NKp44.

As shown in FIG. 1B. RA-FLS express high levels of ULBP-1, ULBP-2 and ULBP3, low levels of MIC-A, and no MIC-B, all known ligands for the activating NK cell receptor NKG2D. Furthermore, RA-FLS express CD155 (poliovirus receptor PVR) and CD48, ligands for DNAM-1 and 2B4, respectively. We did not detect any expression of CD112 (poliovirus-related receptor 2, PRR2), another ligand recognized by DNAM-1. Using Fc fusion proteins of NKp30, NKp44, and NKp46, we detected relatively high expression of a putative NKp44 ligand on RA-FLS, while NKp30-Fc and NKp46-Fc failed to stain these cells. Cells were analyzed by flow cytometry. Filled histograms represent relevant isotype control. Histograms are representative for n≥3 donors.

Figure 1C:
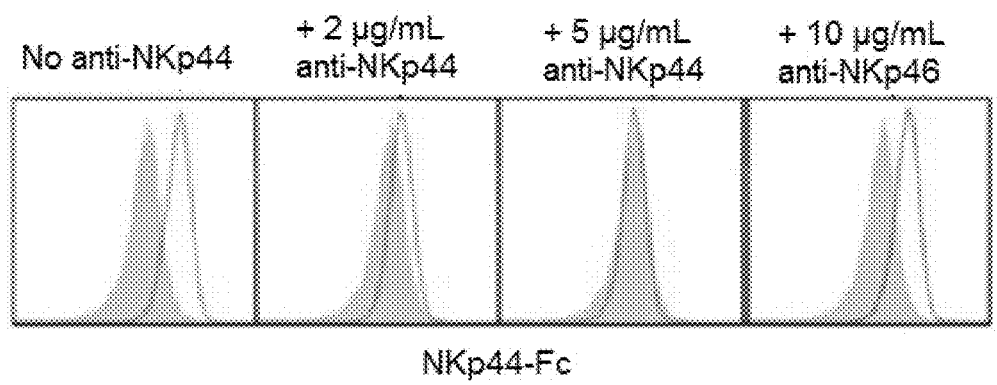
FIG. 1C. shows that an antibody against NKp44 dose-dependently prevents binding of a soluble NKp44-FC fusion protein on RA-FLS suggesting that RA-FLS express a ligand capable of interacting with NKp44 receptors.

FIG. 1C. illustrates that the binding of soluble NKp44-Fc fusion protein to RA-FLS was specific and abolished by the addition of increasing doses of anti-NKp44 mAb. Adherent RA-FLS were detached using 2 mM EDTA, and surface stained with 10 ug/mL NKp44-Fc fusion protein (open histogram) or the same Fc fragment (human IgG1) as a negative control (gray histogram). Where indicated, NKp44-Fc was pre-incubated with anti-NKp44 or anti-NKp46 mAbs.

Figure 1D:
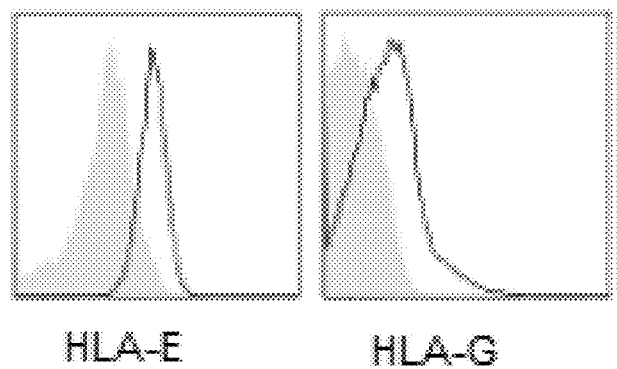
FIG. 1D. shows that RA-FLS express MHC class I ligands HLA-E and HLA-G, ligands known to be recognized by NK cell receptors (e.g. CD94/NKG2A and LIR-1, respectively).

As demonstrated in FIG. 1D., RA-FLS express high levels of both HLA-E and HLA-G, ligands for the inhibitory NK cell receptors CD94-NKG2A and LIR-1, respectively. Thus, HLA-E may be an important molecule protecting RA-FLS from NK cell-mediated cytotoxicity in the inflamed synovium, as most synovial NK cells express the inhibitory CD94-NKG2A receptor.

Figure 1E:
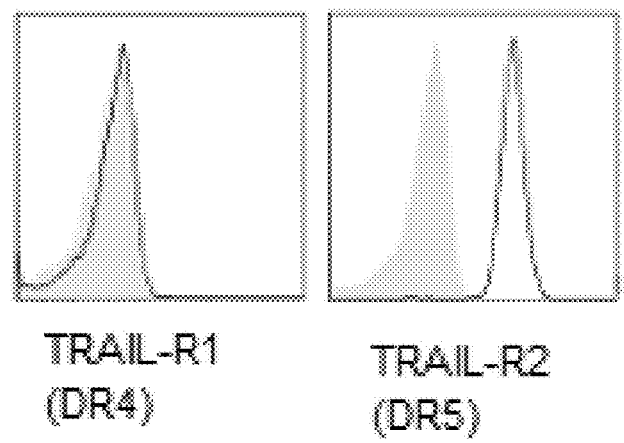
FIG. 1E. shows that RA-FLS express death receptor 5 (DR5) but not DR4, known receptors that bind TRAIL.

In FIG. 1E. it is demonstrated that RA-FLS express death receptor 5 (DR5) but not DR4. These receptors transduce apoptotic signals upon recognition by TRAIL (TNF-related apoptosis-inducing ligand). Thus, DR5 may be an important ligand expressed on RA-FLS that can be recognized by TRAIL expressing cells that potentially can mediate RA-FLS cell death within the inflamed synovial tissue.

Example 2

Figure 2A:
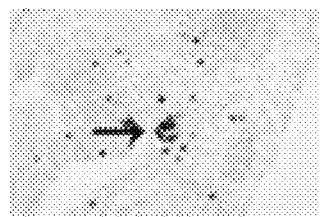
FIG. 2A. shows RA synovial tissue stained with an antibody against human NKp46. The dark stained areas are NKp46 expressing cells.
Figure 2B:
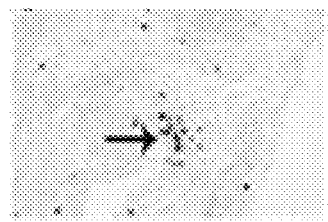
FIG. 2B. shows an adjacent section of the same tissue stained with an antibody against human NKG2A. The dark stained areas are NKG2A expressing cells.
Figure 2C:
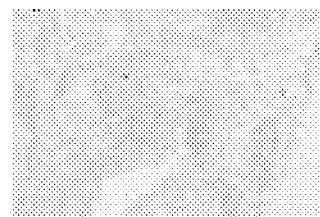
FIG. 2C. shows an adjacent tissue section stained with an isotope control antibody.
Figure 2D:
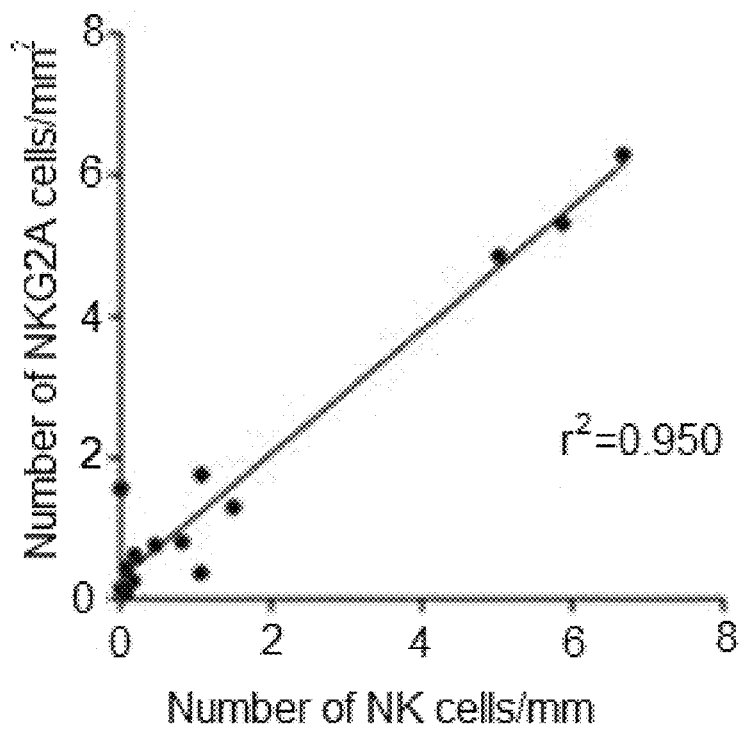
FIG. 2D. shows the frequency of NKG2A+ cells/mm$^2$ synovial tissue plotted against the frequency of NKp46+ cells/mm$^2$ synovial tissue as evaluated by quantitative digital image analysis. The data indicate that most NKG2A+ cells are NK cells in the inflamed RA synovial tissue.

NKG2a Expressing NK Cells are Present in RA Synovium and can be Found in Areas Containing HLA-E Expressing RA-FLS FIGS. 2A, 2B, and 2C shows serial synovial tissue sections derived from a patient with RA stained with mouse anti-NKp46 (NK cells, FIG. 2A), anti-NKG2A (FIG. 2B) and isotype control antibody (FIG. 2C). Immune-specific reactivity was visualized with diaminobenzidine (dark spots in the micrograph) and nuclei were counterstained with hematoxylin (faint spots). The results show that NKp46 NK cells are found in the sublining area and a few closer to the synovial lining of RA synovium (see FIG. 2A). Localization and frequency of NK cells were found to be very similar to that of NKG2A+ cells (see FIG. 2B for comparison). And Sections stained with isotype control were blank (see FIG. 2C). When evaluated by quantitative digital image analysis, the frequency of NKG2A+ cells was found to correlate strongly ($r2=0.950$, $p<0.0001$) with and to match by number that of NK cells, as shown in FIG. 2D.

Figure 2E:
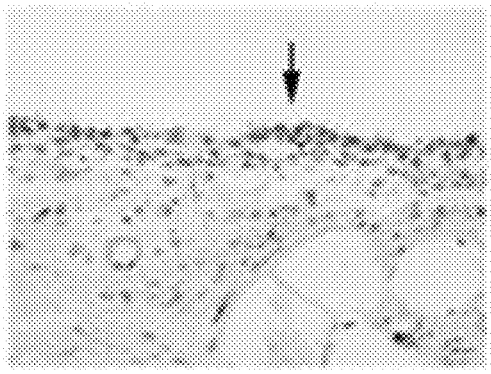
FIG. 2E. shows RA synovial tissue stained with anti-HLA-E antibody. Cells in the synovial lining, including RA-FLS, express HLA-E. The arrow indicates an area of darkly stained HLA-E expressing synovial lining FLS-like cells.
Figure 2F:
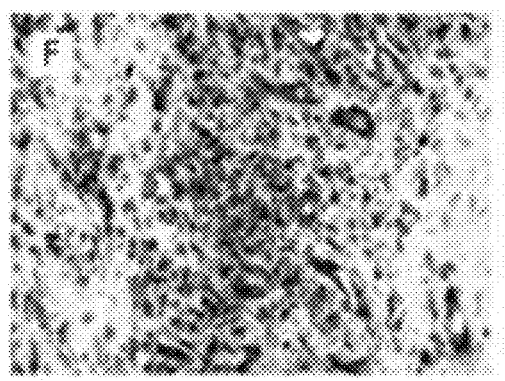
FIG. 2F. shows that infiltrating immune cells in the synovial sublining express HLA-F.
Figure 2G:
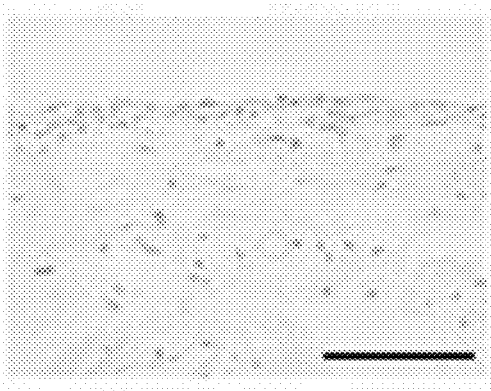
FIG. 2G. shows RA synovial tissue stained with isotype control antibody.
Figure 2H:
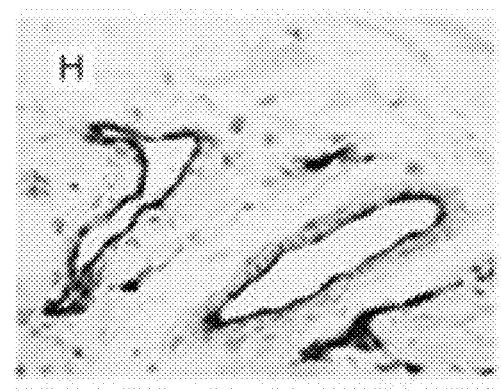
FIG. 2H. shows that vascular endothelial cells express HLA E HLA-E.

The expression of HLA-E, the ligand for CD94-NKG2A, on RA-FLS was evaluated in situ (FIGS. 2E-H). Application of the anti-HLA-E antibody 3D12 onto RA synovial tissue sections revealed staining of the intimal lining, which is made up of macrophage-like synoviocytes (MLS) and RA-FLS, as is shown in FIG. 2E. No staining is observed using an isotype control, as demonstrated in FIG. 2G. Furthermore, both infiltrating immune cells, shown in FIG. 2F, and vascular endothelial cells as shown in FIG. 2H. expressed HLA-E at relatively high levels.

Together, these data show that NK cells can be identified among the infiltrating lymphocyte population in the synovium of RA patients, and suggest that most, if not all, NK cells express NKG2A. Furthermore, subsets of NKG2A+ NK cells are found in areas close to HLA-E+ RA-FLS. Thus, this could potentially mean that NKG2A+ NK cells recognize HLA-E on RA-FLS in situ.

Example 3

Figure 3A:
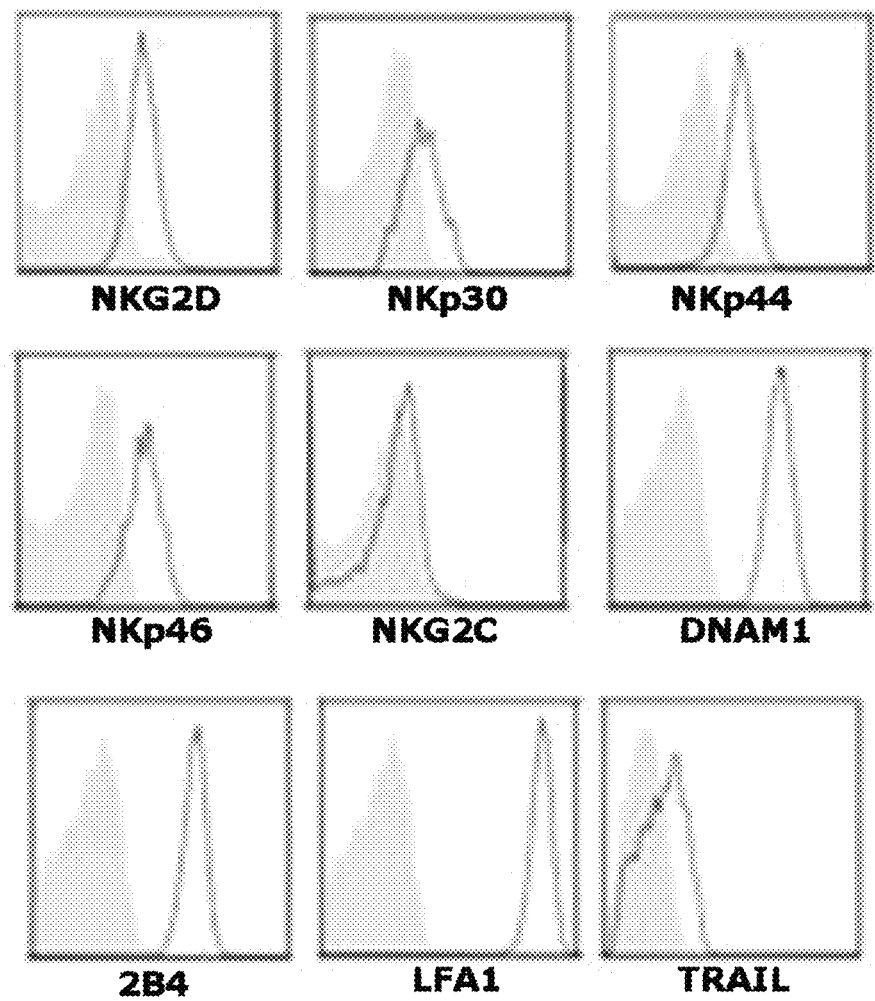
FIG. 3A (i) shows NK cell receptor expression on gated NK cells derived from SFMC of a representative RA patient. Synovial NK cells express NKG2D, NKp30, NKp44, NKp46, DNAM1, 2B4, LFA-1, and TRAIL, but no, or very low levels of NKG2C as indicated by the open histogram overlays.

NKG2D, DNAM-1, NKp44, NKp46, and TRAIL are Involved in NK Cell Cytotoxicity Towards RA-FLS In FIG. 3A. three different types of NK cells that were stained for surface expression of several NK cell receptors are shown (as open histogram), as indicated below each histogram, and staining with a relevant isotype control is also shown in each panel (filled gray histogram). FIG. 3A. (i) shows NK cells derived from SFMC from a representative RA patient, FIG. 3A. (ii) shows resting CD56bright NK cells derived from PBMC from a representative healthy donor and FIG. 3A. (iii) shows Nishi NK cells.

Figure 3B:
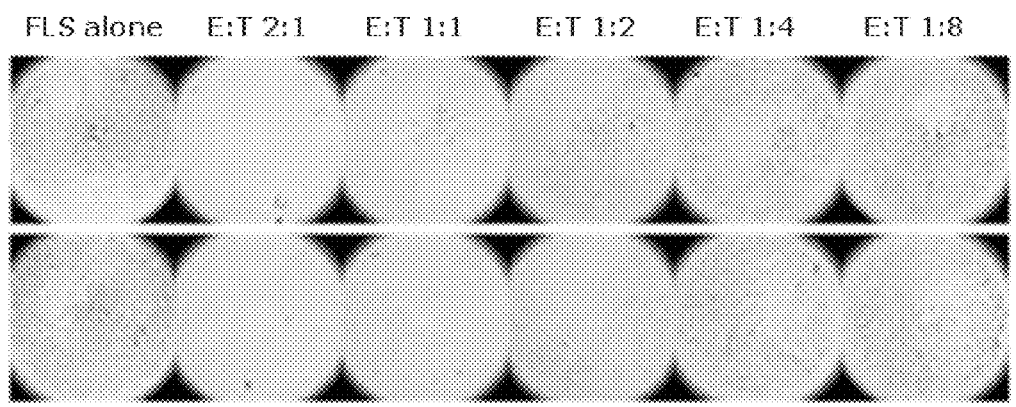
FIG. 3B. shows that NK cells eliminate adherent RA-FLS in vitro.
Figure 3B:
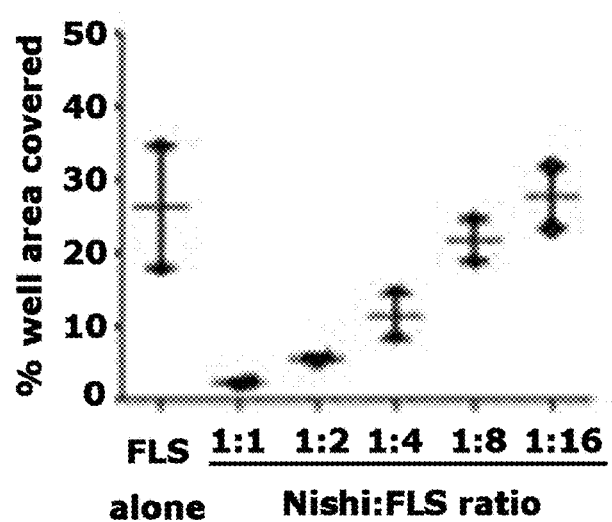

Cells were analyzed by flow cytometry. NK cells were defined as viable CD3-CD56bright. The data shows that synovial NK cells derived from RA patients express several activating receptors, and that they show a similar expression pattern of activating receptors to CD56bright NK cells and Nishi NK cells FIG. 3B. (i) illustrates RA-FLS that were seeded at 10,000 cells/well in 48-well plates, and grown to confluency (~48,000 cells/well) for 72 hours, at which point Nishi were added at the indicated effector:target (E:T) ratios (duplicate wells were set up). RA-FLS and Nishi were co-cultured overnight at 37° C., non-adherent cells were subsequently washed off and adherent cells were fixed with 4% paraformaldehyde and stained with Eosin. An ImmunoSpot Image Analyzer was used to take images and quantify the % well area covered (as shown in FIG. 3B. (ii)).

The data in FIGS. 3B (i) and 3B(ii) shows that NK cells eliminate plastic-adherent RA-FLS in a dose-dependent manner in vitro.

Figure 3C:
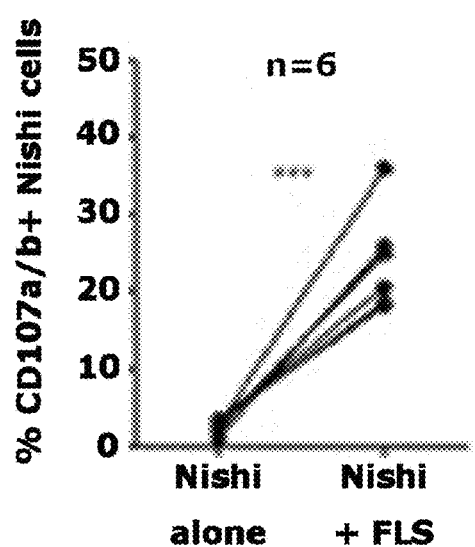
FIG. 3C. shows that NK cells degranulate as measured by CD107a/b cell-surface expression when co-cultured with RA-FLS, but not when cultured alone, indicating that NK cells actively kill RA-FLS.
Figure 3D:
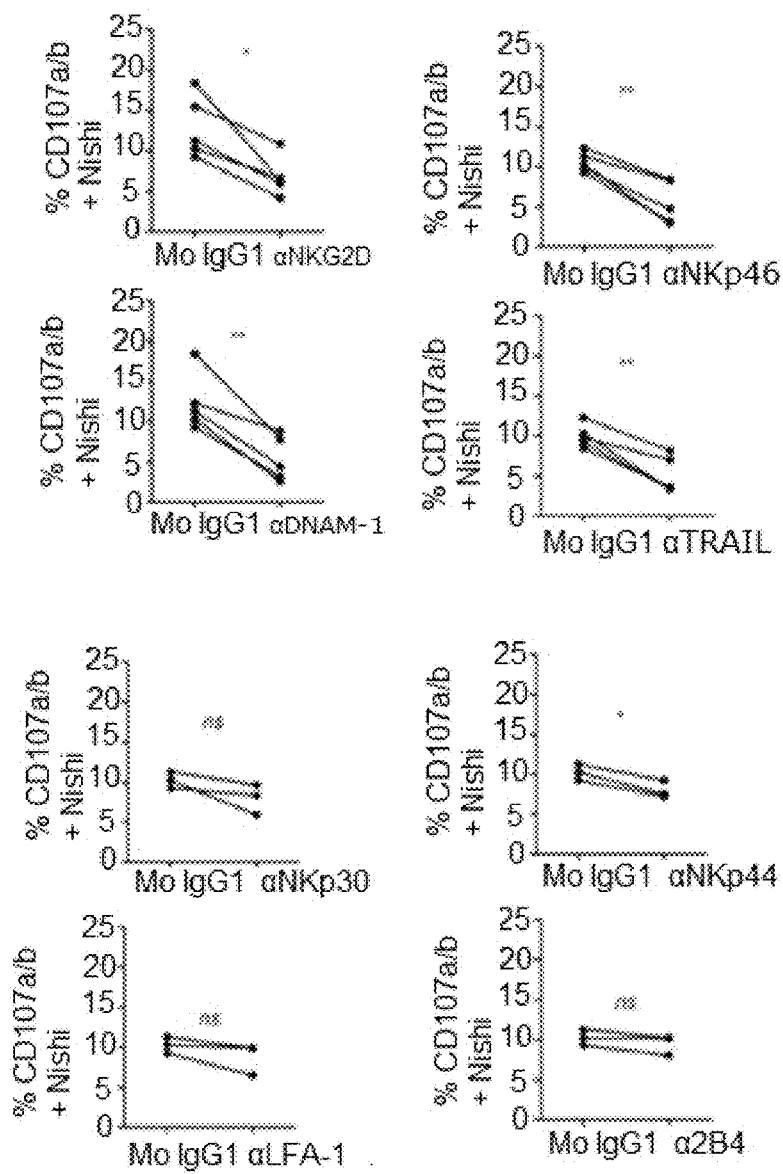
FIG. 3D shows that masking NKG2D, NKp44, NKp46, DNAM-1, or TRAIL expressed by NK cells results in significantly reduced killing of RA-FLS as measured by CD107a/b cell surface expression on effector NK cells.

FIG. 3C. and FIG. 3D (i) demonstrate RA-FLS that were seeded at 30,000 cells/well in 96-well plates, and on the following day 90,000 Nishi/well were added. Nishi and FLS were co-cultured for 5 hours at 37° C. with BD GolgiStop, FITC-conjugated anti-CD107a/b antibodies and 10 ug/mL blocking antibodies, or relevant isotype control, as indicated. Flow cytometry was performed to determine Nishi degranulation. ns=not significant, * $P<0.05$,  $P<0.005$, * $P<0.001$.

FIG. 3C shows that NK cells only degranulate in the presence of FLS target cells and not when cultured alone. FIG. 3D show that RA-FLS are sensitive to NK cell-mediated cytotoxicity, and that NKG2D, DNAM1, NKp44, NKp46 and TRAIL are all involved in the specific recognition of RA-FLS by NK cells as indicated by a significant reduction in CD107a/b expression upon masking such receptors.

Example 4

Figure 4A:
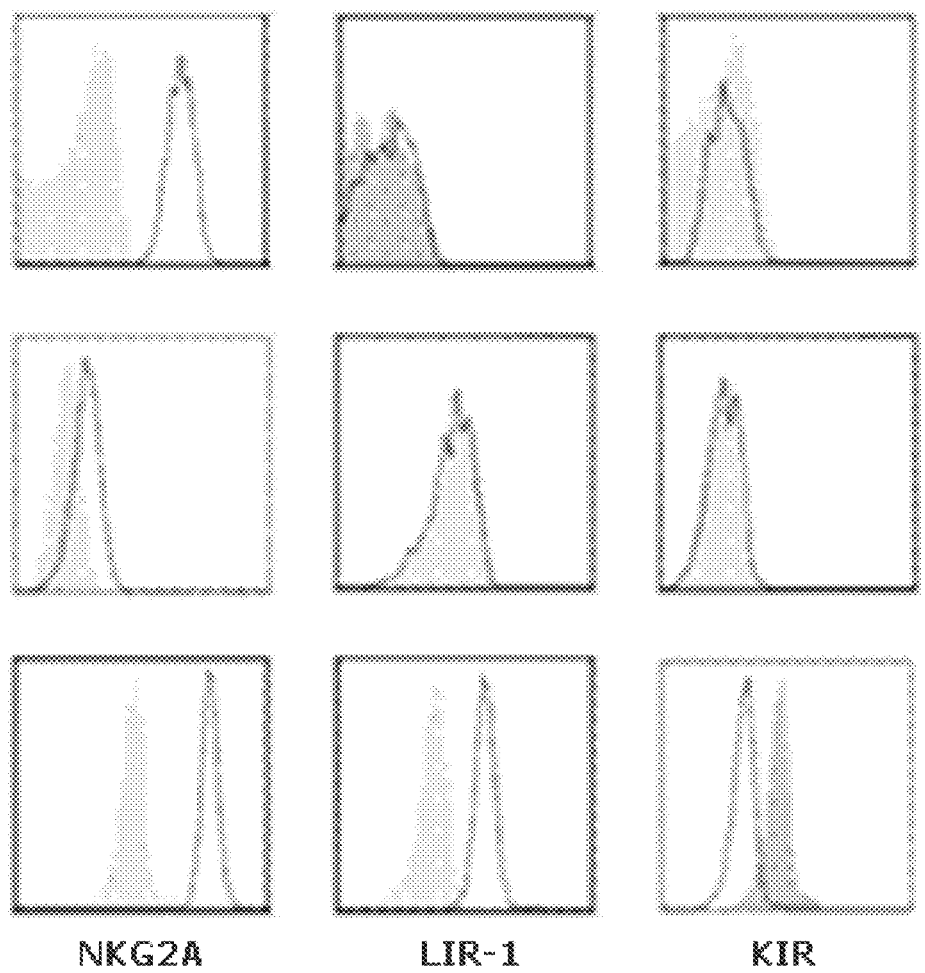
FIG. 4A. shows that RA synovial NK cells (top panel), CD56bright healthy PB-NK cells (middle panel), and Nishi NK cells (bottom panel) all express cell surface NKG2A (left), but lack KIRs (right). In addition, Nishi cells, but not synovial NK cells or CD56bright NK cells, express LIR1 (middle panel)

RA-FLS are Protected from NK Cell-Mediated Cytotoxicity by Expression of HLA-E Capable of Interacting with Inhibitory CD94-NKG2a Receptors Expressed by NK Cells FIG. 4A shows representative histograms with NK cells from RA-SFMC in the top row, resting CD56bright NK cells from healthy PBMC in the middle row and Nishi NK cells in the bottom row. Expression of NKG2A (left column), LIR-1 (middle column) and KIRs (right column) is shown (open histograms) compared with corresponding isotype control (gray filled histograms). NK cells were stained for surface expression using anti-NKG2A, anti-LIR1, and a cocktail of anti-KIR mAbs and subsequently analyzed by flow cytometry. NK cells are gated on viable CD3 negative CD56bright positive cells.

The data show that most synovial fluid NK cells similar to Nishi NK cells and CD56bright PB-NK cells express NKG2A but lack KIRs. In contrast to synovial fluid NK cells, Nishi NK cells also express LIR-1.

Figure 4B:
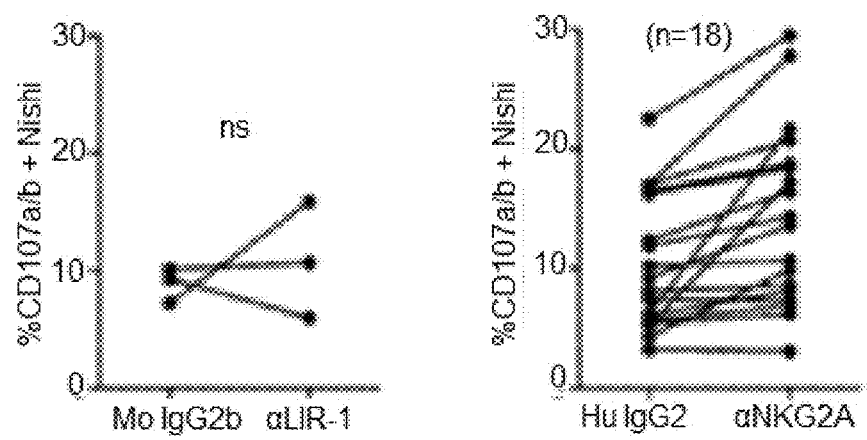
FIG. 4B. shows increased NK cell degranulation as measured by CD107a/b cell-surface expression when NK cells are co-cultured with RA-FLS in the presence of anti-NKG2A (right panel), but not in the presence of anti-LIR1 (left panel).

FIG. 4B illustrates RA-FLS that were seeded at $3 \cdot 10^4$ cells/well in 96-well plates; the following day Nishi were added at an E:T ratio of 3:1 (anti-LIR-1 experiments, left panel) or 6:1 (anti-NKG2A experiments, right panel). Nishi and FLS were co-cultured for 5 hours at 37° C. with BD GolgiStop, FITC-conjugated anti-CD107a/b antibodies and 10 ug/mL blocking antibodies, or relevant isotype control, as indicated. Flow cytometry was performed to determine Nishi degranulation. ns=not significant, ** $P<0.005$, as shown in FIG. 4B.

The data shows that masking NKG2A with an antibody results in a significantly increased NK cell degranulation towards RA-FLS (right panel), while masking L1R-1 does not appear to result in any increased lysis of RA-FLS (left panel). Thus, the fact that anti-NKG2A treatment of NK cells results in increased lysis of RA-FLS indicates that HLA-E molecules expressed on RA-FLS present appropriate peptides important for interacting with CD94-NKG2A inhibitory receptors.

Figure 4C:
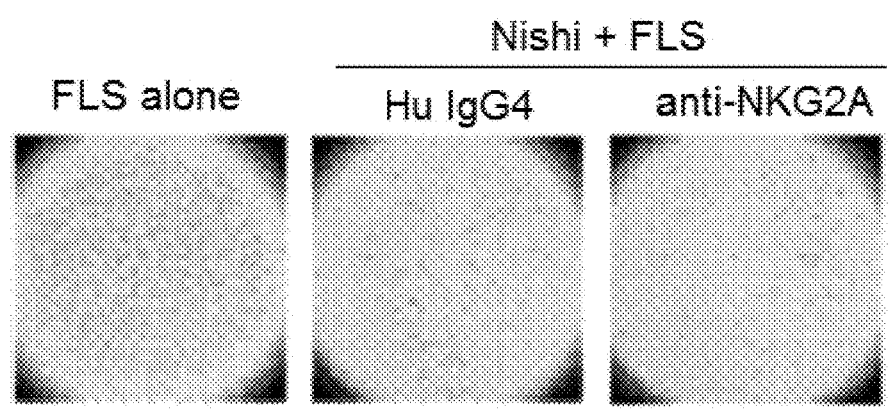
FIG. 4C. shows increased NK cell-dependent clearance of adherent RA-FLS when treated with anti-NKG2A (right image) as compared to treatment with an isotype control (middle image). RA-FLS cultured in the absence of NK cells is shown in the left micrograph image.

FIG. 4C demonstrates RA-FLS that were seeded at $2.4 \cdot 10^4$ cells/well in 96-well plates; the following day $6 \cdot 10^3$ Nishi NK cells/well were added (i.e. E:T of 1:4). FLS and Nishi were co-cultured overnight with the addition of anti-NKG2A or human IgG4 isotype control. The next day, non-adherent cells were washed off, adherent cells were fixed with 4% paraformaldehyde and stained with Eosin. Wells were analyzed, and % well area covered was quantified, using an ImmunoSpot Image Analyzer, as shown in FIG. 4C. Thus, the data show that masking NKG2A results in a significantly increased elimination of adherent RA-FLS.

Figure 4D:
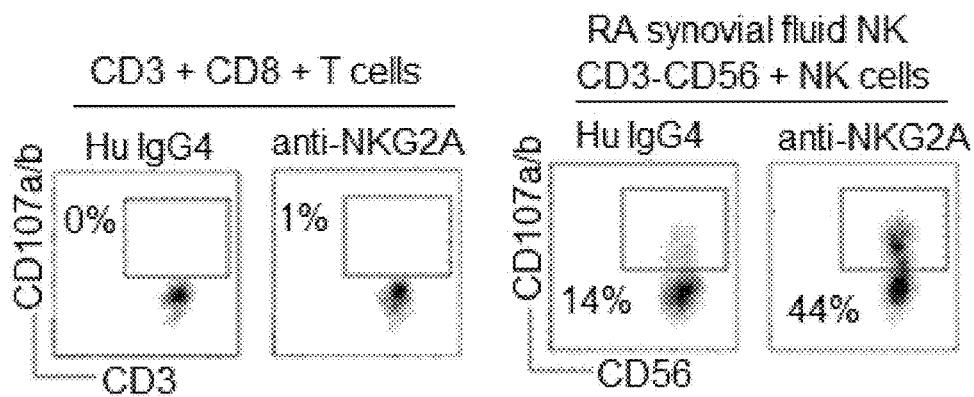
FIG. 4D. shows that synovial NK cells degranulate when co-cultured with autologous RA-FLS (14%, top left) and that masking NKG2A results in increased degranulation (44%, top right). Autologous CD3+ CD8+ T cells do not significantly degranulate when co-cultured with autologous RA-FLS in the absence (i.e. isotype treated cultures, bottom left) or presence (bottom right) of anti-NKG2A.

RA-FLS were seeded at $1.5 \cdot 10^4$ cells/well in 96-well plates; the following day $4.5 \cdot 10^4$ autologous SFMC were added per well (i.e. E:T 3:1). SFMC and RA-FLS were co-cultured for 5 hours at 37° C. with BD GolgiStop, FITC-conjugated anti-CD107a/b antibodies and 10 ug/mL blocking antibodies, or human IgG4 isotype control, as show in FIG. 4D.

Thus, masking NKG2A with mAb results in significantly increased elimination of autologous RA-FLS in vitro, suggesting that therapeutic administration of an anti-NKG2A mAb would result in increased elimination of RA-FLS in vivo.

Figure 4E:
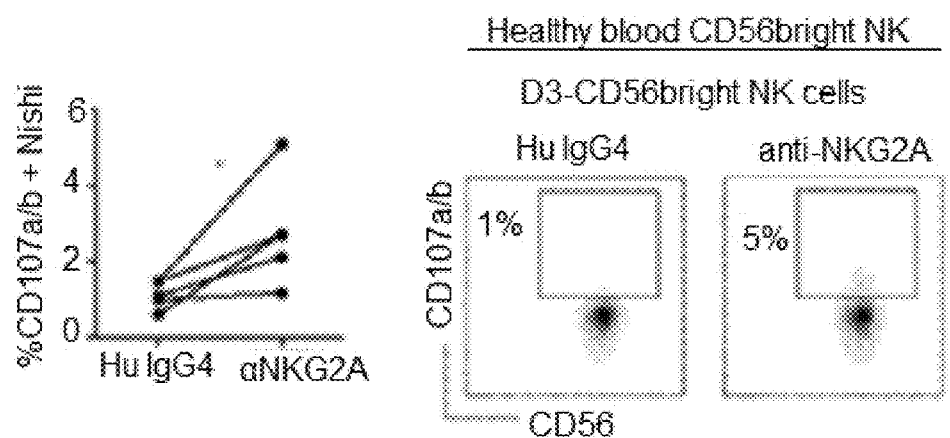
FIG. 4E. shows that freshly isolated and unstimulated CD56bright PB-NK cells from healthy donors degranulate when cocultured with RA-FLS in the presence of anti-NKG2A but minimally so when treated with an isotype control antibody. The top panel shows a representative example and the bottom graph shows the % CD107a/b expression on 5 separate donor CD56bright NK cells co-cultured with RA-FLS in the presence of an isotype vs anti-NKG2A.

FIG. 4E. shows $3 \cdot 10^4$ FLS/well that were seeded in 96-well plates. The following day, allogeneic CD56brightCD16dim NK cells were isolated from healthy donor blood by magnetic separation and immediately co-cultured with RA-FLS (E:T 3:1) for 5 hours at 37° C. with BD GolgiStop, FITC-conjugated anti-CD107a/b antibodies and 10 ug/mL blocking antibodies, or relevant isotype control. Flow cytometry was performed to determine degranulation. NK cells were defined as viable CD3-CD16dimCD56bright. The bottom graph shows CD56bright NK cells from a single healthy donor co-cultured separately with RA-FLS from five different patients. * $P<0.05$.

Thus, masking NKG2A with mAb on resting, freshly isolated PB-NK cells results in significantly increased elimination of allogeneic RA-FLS in vitro, again suggesting that therapeutic administration of an anti-NKG2A mAb would result in increased elimination of RA-FLS in vivo. Thus, aggressive disease spreading RA-FLS that may migrate through the bloodstream to other joints may be eliminated by circulating CD56bright PB-NK cells upon masking their CD94-NKG2A inhibitory receptor.

Figure 5A:
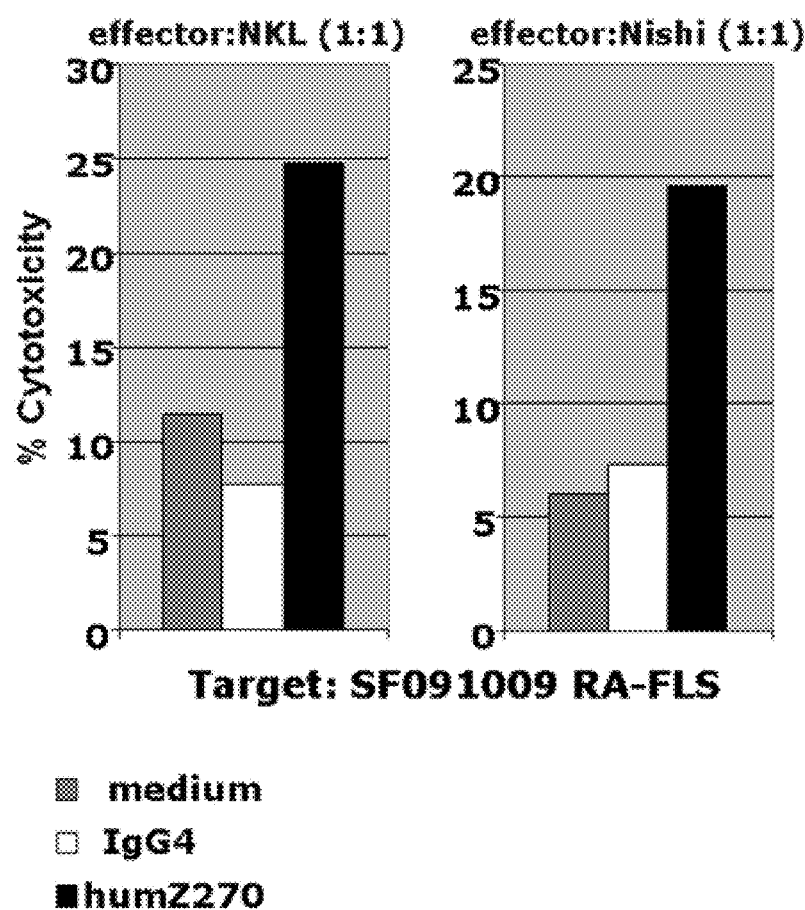
FIG. 5A. shows that blocking NKG2A using NNC141-0100 (humZ270) leads to increased NK cell-mediated elimination of RA-FLS as measured by an LDH release assay. NKL effector cells are shown on the left and Nishi NK cells on the right against a representative RA-FLS target cell.
Figure 5B:
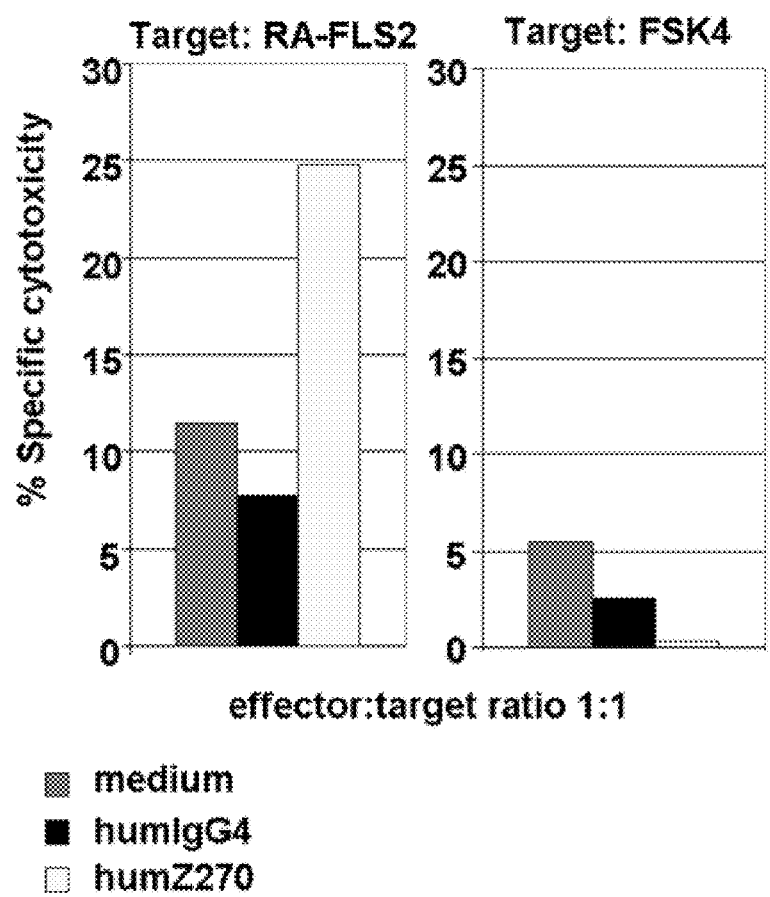
FIG. 5B. shows that blocking NKG2A using NNC141-0100 (humZ270) leads to increased lysis of a representative RA-FLS (RA-FLS2) but does not affect elimination of a normal foreskin fibroblast cell line (FSK4).

FIG. 5A shows an LDH release assay that was employed to assess NK cell-mediated cytotoxicity of FLS using two different NK cell lines (NKL, left; and Nishi, right) in the presence of NNC141-0100 (HumZ270, black bars), isotype control (white bars), or medium alone (gray bars). The NK cell effector to target ratio was 1:1. FIG. 5B shows that blocking NKG2A using NNC141-0100 (humZ270) leads to increased lysis of a representative RA-FLS (RA-FLS2, left panel) but does not affect elimination of a normal foreskin fibroblast cell line (FSK4, right panel). Thus, taken together the data presented in FIG. 3, FIG. 4, and FIG. 5 clearly suggest that anti-NKG2A treatment results in increased NK cell-mediated elimination of RA-FLS while the NK cell-mediated elimination of a normal fibroblast cell line (FSK4) is unaffected in the presence of a blocking antibody (i.e. HumZ270) directed against NKG2A.

Example 6

Figure 6A:
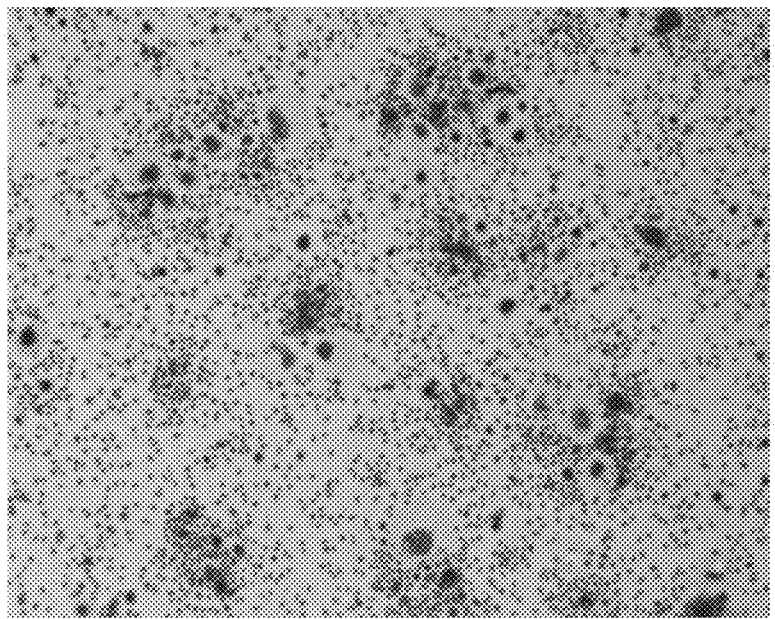
FIG. 6A. shows a representative example of RA-SFMC cultured for 7 days in the presence of humIgG4 isotype. Several large multinucleated TRAP+ cells are visible.

Treatment with humZ270 (Anti-NKG2A) Inhibits Formation of TRAP+ Multi Multinucleated Osteoclasts FIG. 6A shows a representative example where $10^6$ SFMC/well derived from a RA patient were cultured for 7 days in medium supplemented with 10 ng/mL IL-15. Cultures were treated with 20 microgram/ml human IgG4 isotype control (FIG. 6A.) or 20 microgram/ml humZ270 (FIG. 6B.) at the beginning of the assay. It can be appreciated that anti-NKG2A treatment in FIG. 6B results in significant elimination of large plastic adherent multinucleated cells that express TRAP (i.e. defined as osteoclasts).

Figure 6B:
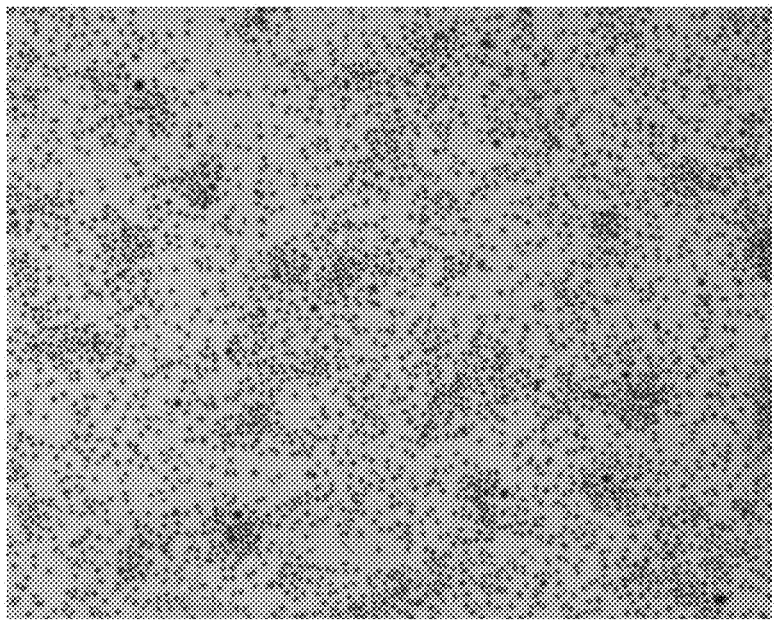
FIG. 6B. shows that humZ270 treatment results in drastically reduced numbers of large multinucleated TRAP+ cells.
Figure 6C:
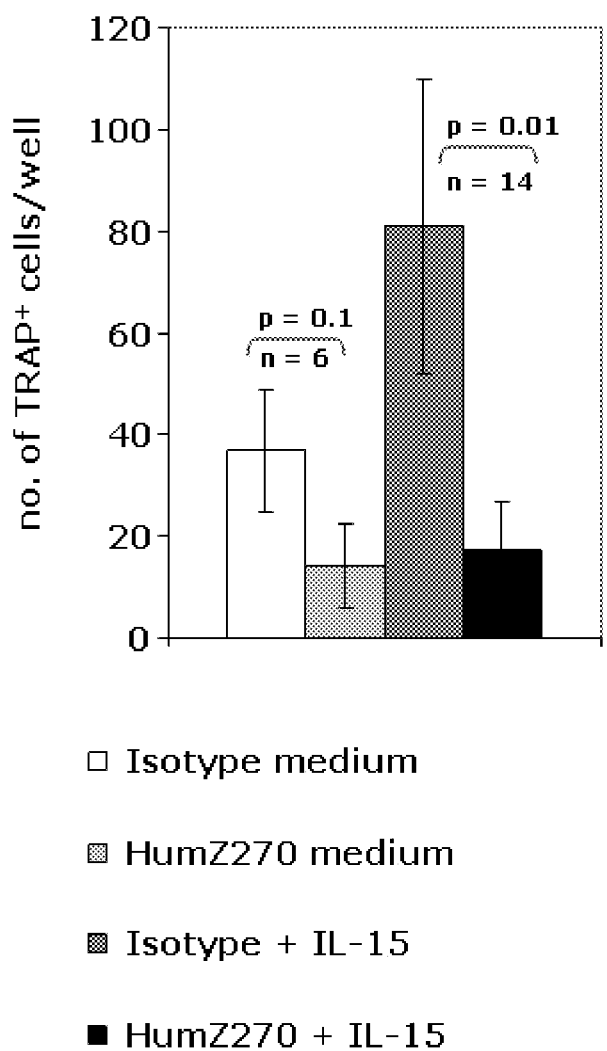
FIG. 6C. shows formation of osteoclasts in SFMC derived from patients with RA cultured in medium or IL-15 in the presence of an isotype control vs anti-NKG2A (humZ270, NNC141-0100) as indicated. Masking NKG2A in cultures stimulated with IL-15 results in reduced number of TRAP+ multinucleated cells.

FIG. 6C. demonstrates the data obtained from SFMC derived from RA patients that have been cultured for 7 days in medium alone (n=6) or medium supplemented with 10 ng/mL IL-15 (n=14). At the beginning of the assay (defined as baseline), 20 microgram/mL human IgG4 isotype (white and dark gray bars) or 20 microgram/mL NNC141-0100 (humZ270, light gray and black bars) were added to the cultures. Osteoclasts were quantitated as numbers of TRAP+ multinuclear cells/well. Thus, taken together FIG. 6A, FIG. 6B, and FIG. 6C shows that treatment with an antibody against NKG2A in SFMC in vitro cultures results in a significant reduction of osteoclast formation as measured by the formation of large multinucleated TRAP+ cells (i.e. osteoclasts). Thus, the findings suggest that therapeutic treatment in RA patients with anti-NKG2A mAb would result in dampening of bone erosion, a major clinical hallmark of RA.

Figure 6D:
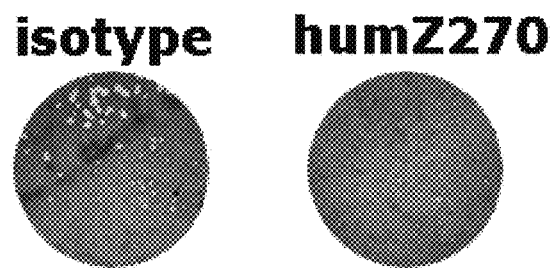
FIG. 6D. shows that formation of bone-mineral eroding osteoclasts in SFMC derived from patients with RA is suppressed by treatment with NNC141-0100. Shown is a representative example of bone mineral erosion observed from an SFMC culture of RA patient no. 2357. SFMC were grown on osteologic discs in the presence of IL-15 and isotype mAb (left) vs anti-NKG2A (humZ270, right). The discs were stained with von Kossa and eroded areas were analyzed using Immunospot S5 Analyzer and appear white against the darker background.

In FIG. 6D a representative example of bone mineral erosion observed from an SFMC culture of RA patient no. 2357 is shown. Here SFMC were grown on discs coated with a thin layer of bone mineral substrate (i.e. osteologic discs) in the presence of IL-15 and isotype mAb (left) vs anti-NKG2A (humZ270, right). The discs were subsequently stained with von Kossa and eroded areas were analyzed using Immunospot S5 Analyzer and appear as light/white areas against the darker background.

Figure 6E:
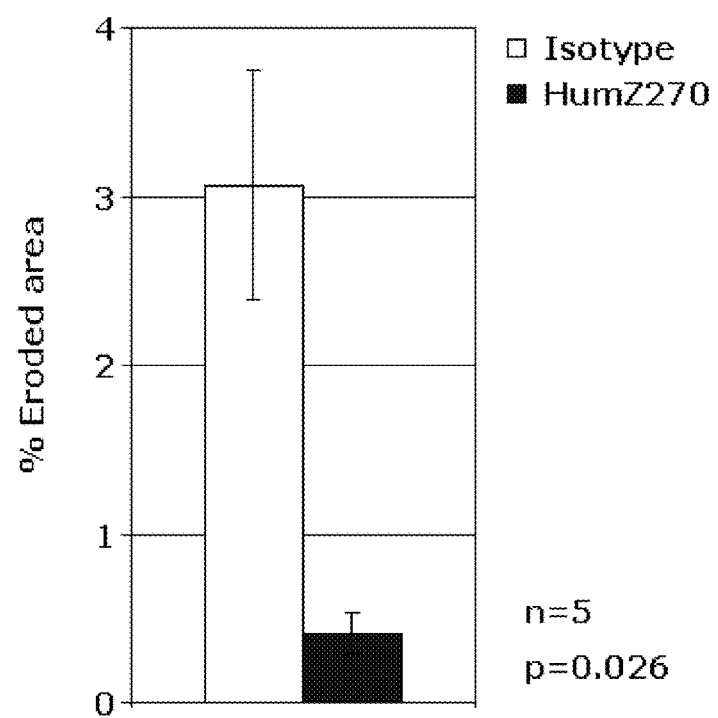
FIG. 6E. SFMC derived from RA patients (n=5) were cultured in medium supplemented with 10 ng/mL IL-15. At the beginning of the assay, 20 microgram/mL human IgG4 isotype (white bar) or 20 microgram/mL NNC141-0100 (humZ270, black bar) were added to the cultures. The mean percentage+/−SEM eroded disc area was quantitated using Immunospot S5 Analyzer.

In FIG. 6E data obtained from in total 5 RA patients is demonstrated. SFMC were cultured in medium supplemented with 10 ng/mL IL-15. At the beginning of the assay, 20 microgram/mL human IgG4 isotype (white bar) or 20 microgram/mL NNC141-0100 (humZ270, black bar) were added to the cultures. The mean percentage+/−SEM eroded disc area was quantitated using Immunospot S5 Analyzer. Taken together, FIG. 6D and FIG. 6E show that anti-NKG2A treatment results in a significant reduction in the formation of active bone mineral eroding osteoclasts. Thus, the findings suggest that therapeutic treatment in RA patients with anti-NKG2A mAb would result in dampening of bone erosion, a major clinical hallmark of RA.

Figure 6F:
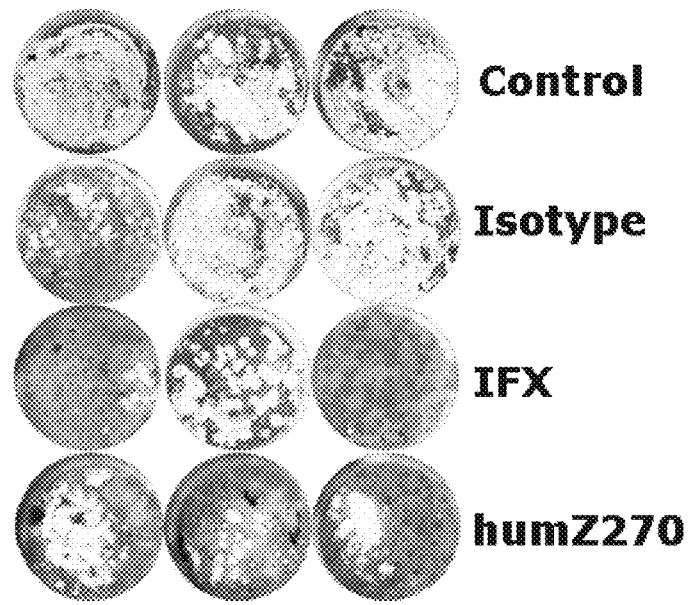
FIG. 6F shows that HumZ270 suppresses bone mineral erosion in RA synovial tissue explant cultures. The figure shows an example where RA synovial tissue shavings were grown in triplicate wells on bone mineral discs in the presence of medium alone (control, top), isotype control (second from top), infliximab (IFX, third from top), or anti-NKG2A (humZ270, bottom). The light areas represent bone mineral erosion.

FIG. 6F illustrates that HumZ270 (anti-NKG2A) suppresses bone erosion in RA synovial tissue explant cultures cultured directly ex vivo. RA synovial tissue shavings were grown for 7 days in IMDM medium supplemented with 10% FBS, 2% HuS, P/S, L-glut without addition of mAbs (control) or with addition of isotype, infliximab (IFX), or anti-NKG2A (humZ270), all mAbs at 10 micrograms/mL added in the beginning of the culture. The experiment was set up in triplicate wells. At day 7, the medium and cells were removed by rinsing the wells 3× with 200 uL Milli-Q™ water. The discs were subsequently rinsed with 200 uL bleach solution (~6% NaOCl, ~5.2% NaCl) for 5 minutes followed by gentle pipetting to dislodge any remaining cells. Finally, the discs were washed 3× with Milli-Q™ water, air-dried and stained with the von Kossa method. It can be appreciated from this example of triplicate cultures that humZ270 treatment of RA synovial tissue explants results in decreased erosion (light/white areas) as compared to control or isotype treated cultures.

Figure 6G:
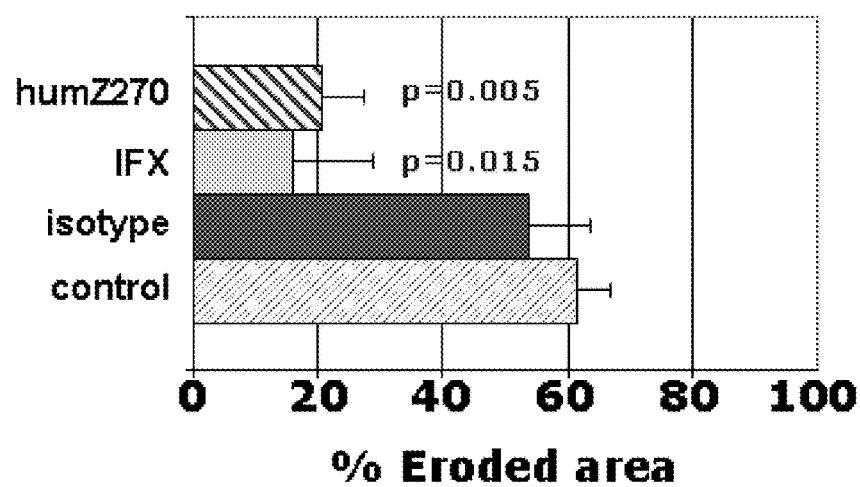
FIG. 6G. shows percentage bone mineral erosion observed as determined by analysis using an Immunospot analyzer.

In FIG. 6G the calculated results (mean+/−SEM) from triplicate cultures of RA synovial tissue shavings that have been grown for 7 days in IMDM medium supplemented with 10% FBS, 2% HuS, P/S, L-glut without addition of mAbs (control) or with addition of isotype, infliximab (IFX), or anti-NKG2A (humZ270), all mAbs at 10 micrograms/mL added in the beginning of the culture, are illustrated. At day 7, the medium and cells were removed by rinsing the wells 3× with 200 uL MILLI-Q water. The discs were subsequently rinsed with 200 uL bleach solution (~6% NaOCl, ~5.2% NaCl) for 5 minutes followed by gentle pipetting to dislodge any remaining cells. Finally, the discs were washed 3× with MilliQ™ water, air-dried and stained with the von Kossa method. HumZ270 treatment of RA synovial tissue explants results in significantly decreased erosion (p=0.005, Student's T test) as compared to control or isotype treated cultures. Thus, RA tissue growing directly ex vivo on discs coated with bone minerals (i.e. osteologic discs) show significant erosive capacity and such activity is drastically inhibited by treatment with anti anti-NKG2A, clearly suggesting that therapeutic treatment in RA patients with anti-NKG2A would suppress bone erosion, a major clinical hallmark of RA.

Example 7

Modulation of Cytokine Levels in SFMC In Vitro Cultures Upon Treatment with HumZ270 (NNC141-0100)

Figure 7A:
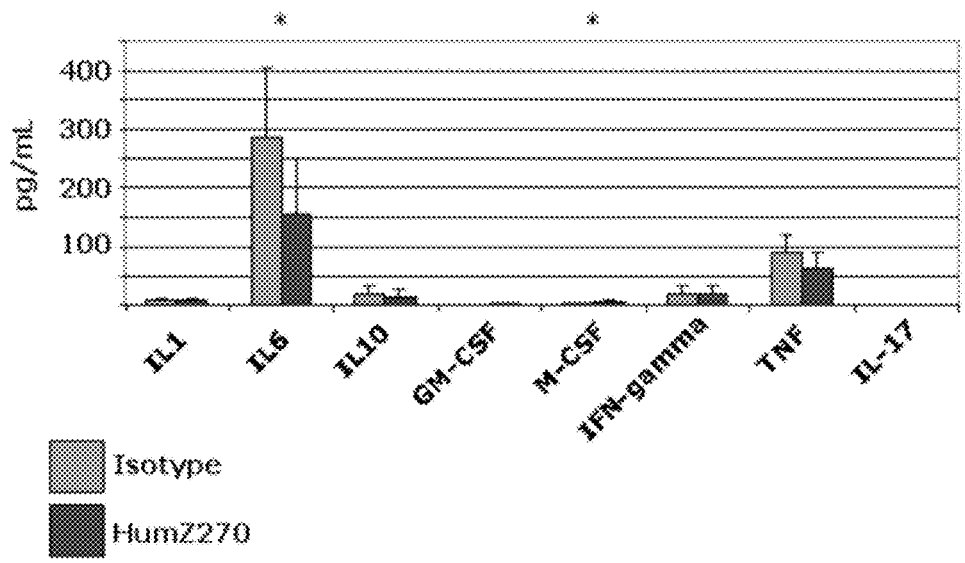
FIG. 7A. shows modulation of cytokine levels as measured at 24 hrs in SFMC in vitro cultures upon treatment with humZ270 (NNC141-0100, dark gray bars) as compared to an isotype control (light gray bars). A significant reduction in IL6 levels is observed upon masking NKG2A. In addition, a slight increase in M-CSF is observed.

In FIG. 7A modulation of cytokine levels (mean+/−SEM) in in vitro cultures of SFMC derived from patients with RA (n=11) is demonstrated. SFMC were cultured for 7 days in medium supplemented with 10 ng/mL IL-15. Cultures were treated with 20 micrograms/mL human IgG4 isotype (light gray bars) or 20 micrograms/mL NNC141-0100 (humZ270, dark gray bars) at the beginning of the assay. Supernatant was harvested at 24 hours and the levels of cytokines was measured by BioPlex. The IL-6 levels are significantly reduced upon treatment with anti-NKG2A, while the production of other cytokines is not significantly affected, except for a small increase in M-CSF at 24 hours.

Figure 7B:
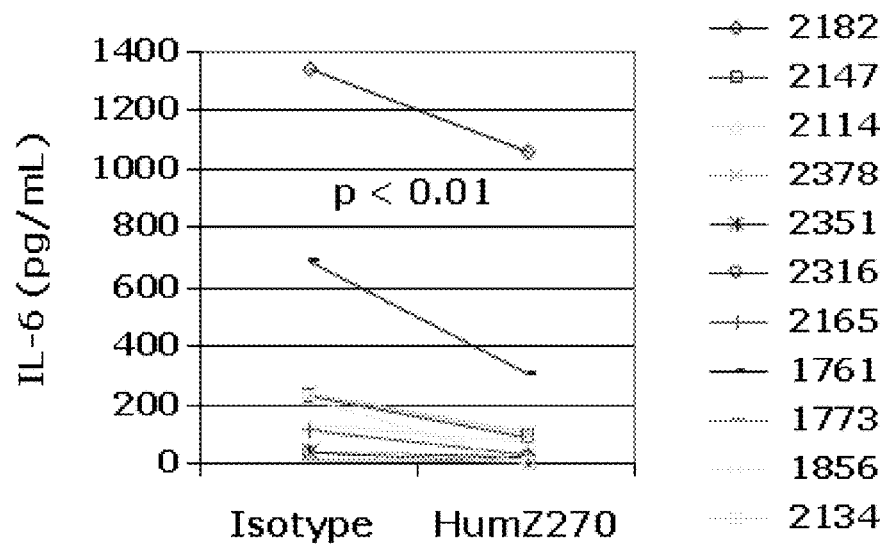
FIG. 7B. shows a pairwise comparison of IL-6 levels produced in the presence of anti-NKG2A (NNC141-0100, humZ270) vs isotype control in RA-SFMC cultures (n=11).

FIG. 7B shows a pairwise comparison between the IL-6 levels measured in RA-SFMC in vitro cultures stimulated with IL-15 and treated with isotype vs HumZ270 (anti-NKG2A). The IL-6 levels are significantly reduced upon masking NKG2A in all SFMC in vitro cultures.

Figure 7C:
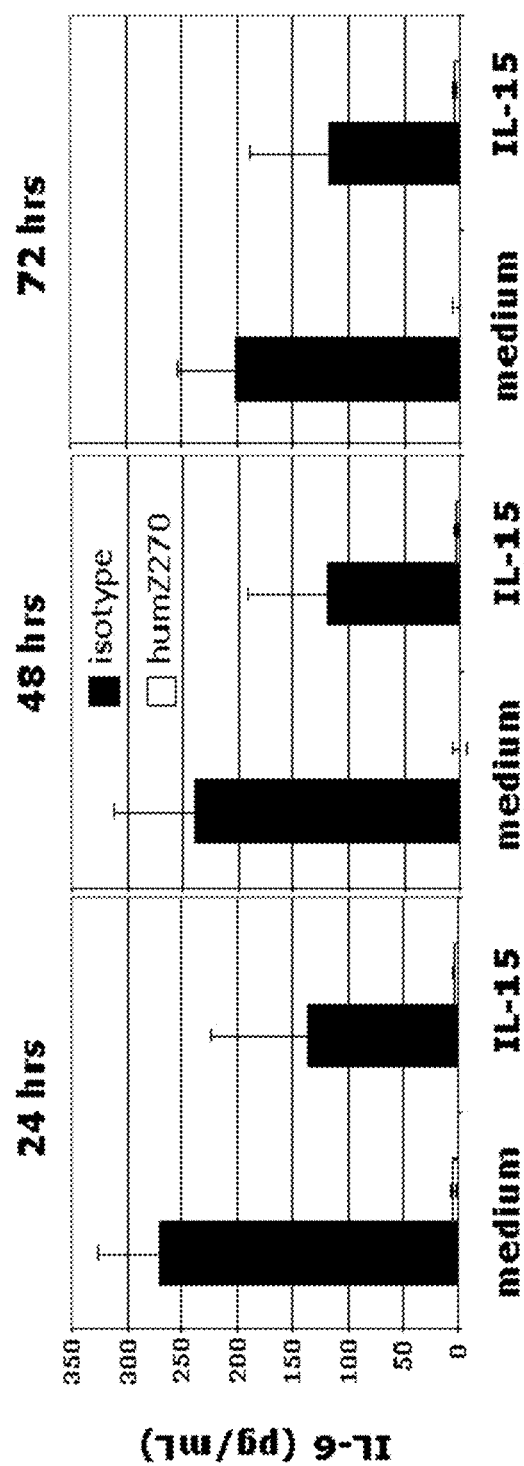
FIG. 7C. shows that anti-NKG2A inhibits both baseline (i.e. medium alone) and IL-15 stimulated IL-6 production in ex vivo cultures of SFMC derived from patients with RA. Mean and SD of two representative RA patients are shown.

In FIG. 7C it is demonstrated that NNC141-0100 (humZ270) inhibits both baseline and IL-15 stimulated IL-6 production in in vitro cultures of SFMC derived from patients with RA. IL-6 levels produced by SFMC derived from 2 patients with RA were measured in cultures established in medium alone or medium supplemented with 10 ng/mL IL-15 as indicated. Cultures were treated with 20 micrograms/mL human IgG4 isotype (black bars) or 20 micrograms/mL NNC141-0100 (humZ270, white bars) at the beginning of the assay. Supernatant was harvested at 24, 48 and 72 hours and the levels of IL-6 were measured by BioPlex. Taken together, FIGS. 7A, 7B, and 7C show that anti-NKG2A suppresses both baseline and stimulated IL-6 levels in SFMC in vitro cultures. IL-6 is an important pro-inflammatory cytokine involved in the RA pathogenesis. Potentially, the reduction in IL-6 plays a role in the observed reduction in osteoclast formation.

Example 8

NKG2a and/or its Ligand HLA-E is Expressed in Inflamed Synovium from RA, Osteoarthritis (OA) and Psoriatic Arthritis (PsA) Patients NK cells present in RA synovial tissue express the inhibitory NKG2A receptor and are localized predominantly in lymphoid aggregates adjacent to synoviocytes that express HLA-E, the ligand for CD94-NKG2A. This is shown in FIG. 8. where representative pictures of RA synovial tissue from two out of 15 donors are depicted (ID 1144-09: A, C, E, G, I and ID 1591-08: B, D, F, H, J). Serial sections of RA synovium were stained for NK cells with an anti-NKp46 antibody (FIGS. 8A. and 8B), for NKG2A with the 2199 antibody (FIGS. 8C. and 8D.), for HLA-E with the 3D12 antibody (FIGS. 8E. and 8F.) and for T cells with an anti-CD3 antibody (FIGS. 8G. and 8H.). No staining was observed using an IgG2b isotype control antibody (FIGS. 8I. and 8J.). Immune-specific reactivity was visualized with diaminobenzidine (DAB) and nuclei were counterstained with hematoxylin (bars=100 Arrowheads indicate lymphoid aggregates in sublining tissue with NKp46, NKG2A, HLA-E and CD3 expressing cell subsets. Arrows indicate HLA-E$^+$ synoviocytes in hyperplastic synovial lining layer adjacent to lymphoid aggregates with NK cells. Asterisks indicate HLA-E$^+$ vascular endothelial cells.

Figure 8M:
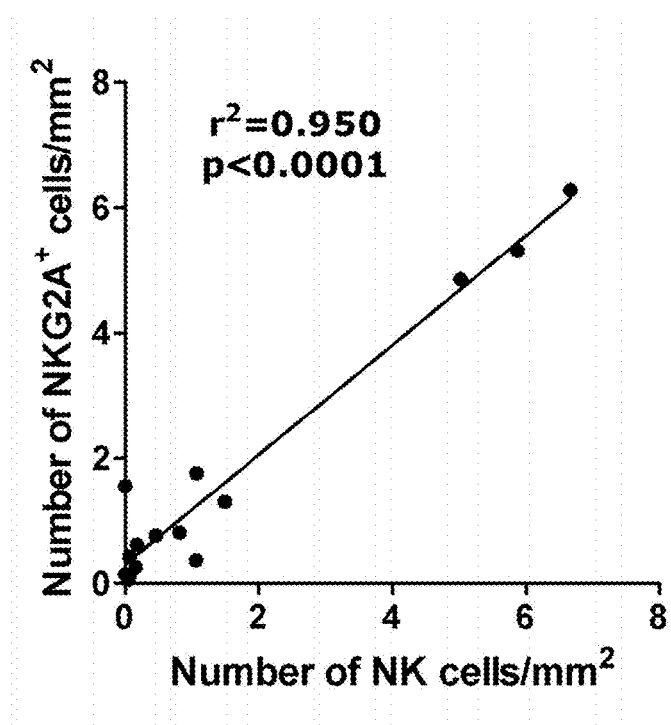
FIG. 8. shows that NK cells present in RA synovial tissue express the inhibitory NKG2A receptor and are localized predominantly in lymphoid aggregates adjacent to synoviocytes that express HLA-E, the ligand for CD94-NKG2A.

High magnification pictures of NKp46$^+$ NK cells (FIG. 8K.) and NKG2A$^+$ cells (FIG. 8L.) in serial sections of RA synovium from a third donor (ID 1595-08) are shown to emphasize that the localization and frequency of NK cells were very similar to that of NKG2A$^+$ cells. Digital image analysis was used to correlate the number of NKG2A$^+$ cells in synovium from 15 RA patients with the number of NKp46$^+$ NK cells (FIG. 8M.). Results are expressed as number of cells per mm$^2$ and show that the frequency of NKG2A+ cells strongly correlates with ($r^2$=0.950, p<0.0001) and matches by number that of NK cells. NKG2A$^+$ cells were present in the synovium of 13/15 RA patients.

Together, these data show that NK cells can be identified among the infiltrating lymphocyte population in the synovium of RA patients, and suggest that most, if not all, NK cells express NKG2A. The ligand for CD94-NKG2A, HLA-E, is expressed by many infiltrating immune cells, vascular endothelial cells and synoviocytes (macrophage-like synoviocytes (MLS) and RA-FLS). Subsets of NKG2A+NK cells are found in areas close to HLA-E+ synoviocytes. Thus, this could potentially mean that NKG2A+NK cells recognize HLA-E on RA-FLS in situ. Moreover, HLA-E+ infiltrating immune cells and vascular endothelium may also be recognized by NKG2A+ NK cells.

Figure 9A:
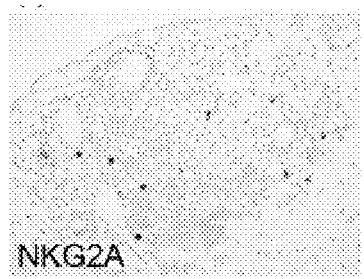
Figure 9B:
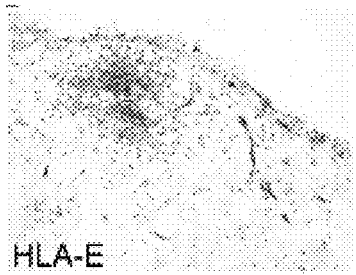
Figure 9C:
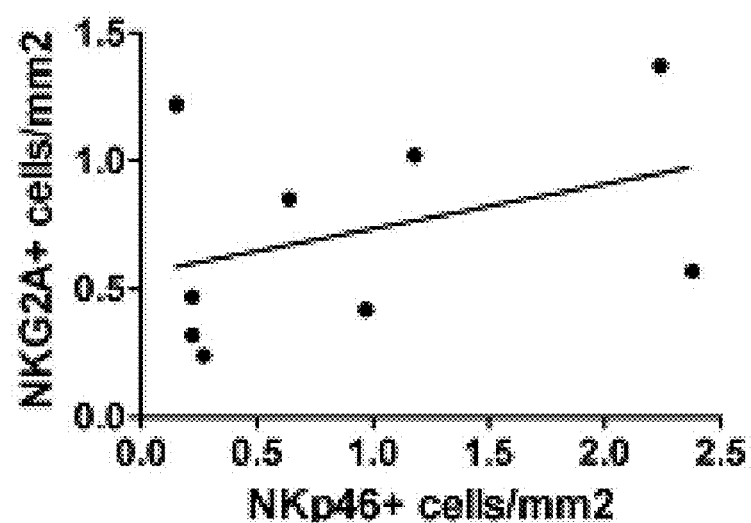

NKG2A and its ligand, HLA-E, are expressed in synovium of patients with osteoarthritis (OA). This is shown in FIG. 9., which depicts NKG2A+ cells (Z199 antibody) among infiltrating lymphocytes (FIG. 9A.) and HLA-E expression (3D12 antibody) by infiltrating immune cells, endothelial cells and synoviocytes (FIG. 9B.). NKG2A+ cells were present in the synovium of 6/9 OA patients. In contrast to RA patients, the frequency of NKG2A+ cells does not seem to correlate with that of NK cells in OA synovium, when quantified by digital image analysis ($r^2$=0.136, p=0.3295; FIG. 9C.), indicating that some of the NK cells that infiltrate OA synovium may not express NKG2A.

Together, these data show expression of NKG2A and HLA-E in OA synovial cell subsets similar to those of RA synovium. Thus, NKG2A+NK cells may recognize HLA-E+ synoviocytes, vascular endothelium and infiltrating immune cells in inflamed synovium of OA patients.

The ligand for CD94-NKG2A, HLA-E, was found to be expressed in inflamed synovium from not only RA and OA, but also psoriatic arthritis (PsA) patients. This is shown in FIG. 10. which depicts staining of synovial tissue samples from RA, OA and PsA patients (as indicated) with the anti-HLA-E antibody mAb MEM-E/02. In synovium of normal controls, HLA-E expression is observed in vascular endothelium and, more weakly, in subsets of synoviocytes located in the synovial lining, as indicated in FIG. 10.

These data show expression of HLA-E by synoviocytes, vascular endothelium and infiltrating immune cells in inflamed synovium of PsA patients, meaning that NKG2A+ cells may recognize such HLA-E+ cell subsets in these patients.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EMBODIMENTS

1. An anti-NKG2A antibody, or an antigen binding fragment thereof, for the treatment of cartilage destruction and/or bone erosion.
2. An anti-NKG2A antibody, or an antigen binding fragment thereof, according to embodiment 1, for the treatment of a disease or disorder where reduction of cartilage destruction and/or bone erosion is beneficial to the patient.
3. An anti-NKG2A antibody, or an antigen binding fragment thereof, according to embodiment 1 or 2, wherein said anti-NKG2A antibody stimulates selective elimination of cartilage destructive cells and/or reduces formation of bone eroding cells.
4. An anti-NKG2A antibody, or an antigen binding fragment thereof, according to any of the preceding embodiments, wherein selective elimination of cartilage destructive cells and/or reduction of bone erosive cells is beneficial to the patient.
5. An anti-NKG2A antibody, or an antigen binding fragment thereof, according to any of the preceding embodiments, wherein the cartilage destructive cells are fibroblast-like synoviocytes (FLS).
6. An anti-NKG2A antibody, or an antigen binding fragment thereof, according to any of embodiments 1-5, wherein the bone eroding cells are osteoclasts.
7. An anti-NKG2A antibody, or an antigen binding fragment thereof, according to embodiment 6, wherein the bone eroding osteoclasts are TRAP+ multinucleated cells.
8. An anti-NKG2A antibody, or antigen binding fragment thereof, according to any of the preceding embodiments, for the treatment of a disease or disorder characterised by cartilage destruction and/or bone erosion.
9. An anti-NKG2A antibody, or an antigen binding fragment thereof, according to embodiment 8, wherein the disease or disorder is osteoarthritis.
10. An anti-NKG2A antibody, or an antigen binding fragment thereof, according to embodiment 8, wherein the disease or disorder is osteoporosis.
11. An anti-NKG2A antibody, or an antigen binding fragment thereof, according to embodiment 8, wherein the disease or disorder is psoriatic arthritis.
12. An anti-NKG2A antibody, or an antigen binding fragment thereof, according to embodiment 8, wherein the disease or disorder is rheumatic arthritis.
13. An anti-NKG2A antibody, or an antigen binding fragment thereof, according to any of the preceding embodiments, wherein said antibody is an antigen binding fragment thereof.
14. An anti-NKG2A antibody, or an antigen binding fragment thereof, according to embodiment 13, wherein the antibody fragment is selected from a Fab, a Fab', a F(ab)$_2$, a F(ab')$_2$, a F(ab)$_3$, an Fv, a single-chain Fv, a dsFv, an Fd fragment, a dAb fragment, a minibody, a diabody, a triabody, a tetrabody, a kappa body, a camel IgG, an IgNAR, and a multispecific antibody fragment.
15. An anti-NKG2A antibody, or an antigen binding fragment thereof, according to any of the preceding embodiments, wherein said antibody is a Fab fragment.
16. An anti-NKG2A antibody, or an antigen binding fragment thereof, according to any of the preceding embodiments, wherein said antibody is a bispecific antibody.
17. An anti-NKG2A antibody, or an antigen binding fragment thereof, according to any of the preceding embodiments, wherein said antibody is conjugated to a half-life extending moiety.
18. An anti-NKG2A antibody, or an antigen binding fragment thereof, according to any of the preceding embodiments, wherein said half-life extending moiety comprises one or more half-life extending moieties selected from one or more of the list consisting of: fatty acids and derivatives thereof, Hydroxyethyl Starch (HES), Polyethylene Glycol (PEG), hyaluronic acid (HA), heparosan polymers, Phosphorylcholine-based polymers, fleximers, dextran, poly-sialic acids (PSA), an Fc domain, transferrin, albumin, Elastin-like peptides, XTEN polymers, albumin binding peptides, and any combination thereof.

19. An anti-NKG2A antibody, or an antigen binding fragment thereof, according to embodiment 18, wherein the antibody can be conjugated with two or more different types of half-life extending moieties.
20. An anti-NKG2A antibody, or an antigen binding fragment thereof, according to any of the preceding embodiments, wherein said antibody comprises a mutated Fc domain, wherein said mutations result in reduced Fcγ receptor binding functions.
21. An anti-NKG2A antibody, or an antigen binding fragment thereof, according to embodiment 20, wherein said Fc domain comprises one or more of the following mutations: L234A, L235E, and G237A, A330S and P331S (according to the Kabat numbering scheme).
22. An anti-NKG2A antibody, or an antigen binding fragment thereof, according to any of the preceding embodiments, wherein said antibody comprises an IgG4 Fc domain.
23. An anti-NKG2A antibody, or an antigen binding fragment thereof, according to embodiment 22, wherein said IgG4 Fc domain comprises the S241P/S228P mutation.
24. An anti-NKG2A antibody, or an antigen binding fragment thereof, according to any of the preceding embodiments, wherein said antibody is a full-length IgG4 antibody or fragment thereof.
25. An anti-NKGA antibody, or an antigen binding fragment thereof, according to any of the preceding embodiments, wherein said antibody is a humanized or human antibody.
26. An anti-NKG2A antibody, or an antigen binding fragment thereof, according to embodiment 25, wherein said antibody is humZ270 or humZ199.
27. An anti-NKG2A antibody, or an antigen binding fragment thereof, according to embodiment 25 or 26, wherein said antibody is humZ270.
28. An anti-NKG2A antibody, or an antigen binding fragment thereof, according to any of embodiments 25-27, wherein the heavy chain of said antibody comprises:
    a CRD1 sequence of amino acid residues 31 to 35 (SYWMN) of SEQ. ID. NO:2, wherein one or two of these amino acid residues may be substituted by a different amino acid residue; and/or
    a CRD2 sequence of amino acids 50-59 (RIDPYDSETH) of SEQ. ID. NO: 2, wherein one, two or three of these amino acid residues may be substituted by a different amino acid residue; and/or
    a CDR3 sequence of amino acids 95-102 (YCARGGYD) of SEQ. ID. NO: 2, wherein one, two or three of these amino acid residues may be substituted by a different amino acid.
29. An anti-NKG2A antibody, or an antigen binding fragment thereof, according to any of embodiments 25-28, wherein the light chain of said antibody comprises:
    a CDR1 sequence of amino acid residues 24-34 (RASENIYSYLA) of SEQ. ID. NO: 3, wherein one, two or three of these amino acid residues may be substituted with a different amino acid; and/or
    a CDR2 sequence of amino acid residues 50-56 (NAKTLAE) of SEQ. ID. NO: 3, wherein one or two of these amino acid residues may be substituted with a different amino acid; and/or
    a CDR3 sequence of amino acid residues 89-97 (QHHYGTPRT) of SEQ. ID. NO: 3, wherein one two or three of these amino acid residues may be substituted with a different amino acid.
30. An anti-NKG2A antibody, or an antigen binding fragment thereof, according to any of embodiments 25-29, wherein the heavy chain of said antibody comprises:
    a CRD1 sequence of amino acid residues 31 to 35 (SYWMN) of SEQ. ID. NO:2; and/or
    a CRD2 sequence of amino acids 50-59 (RIDPYDSETH) of SEQ. ID. NO: 2; and/or
    a CDR3 sequence of amino acids 95-102 (YCARGGYD) of SEQ. ID. NO: 2.
31. An anti-NKG2A antibody, or an antigen binding fragment thereof, according to any of embodiments 25-30, wherein the light chain of said antibody comprises:
    a CDR1 sequence of amino acid residues 24-34 (RASENIYSYLA) of SEQ. ID. NO: 3; and/or
    a CDR2 sequence of amino acid residues 50-56 (NAKTLAE) of SEQ. ID. NO: 3; and/or
    a CDR3 sequence of amino acid residues 89-97 (QHHYGTPRT) of SEQ. ID. NO: 3.
32. An anti-NKG2A antibody, binding fragment thereof, according to any of embodiments 25-31, wherein the heavy chain of said antibody comprises:
    a CRD1 sequence of amino acid residues 31 to 35 (SYWMN) of SEQ. ID. NO:2; and/or
    a CRD2 sequence of amino acids 50-59 (RIDPYDSETH) of SEQ. ID. NO: 2; and/or
    a CDR3 sequence of amino acids 95-102 (YCARGGYD) of SEQ. ID. NO: 2; and wherein the light chain of said antibody comprises:
    a CDR1 sequence of amino acid residues 24-34 (RASENIYSYLA) of SEQ. ID. NO: 3; and/or
    a CDR2 sequence of amino acid residues 50-56 (NAKTLAE) of SEQ. ID. NO: 3; and/or
    a CDR3 sequence of amino acid residues 89-97 (QHHYGTPRT) of SEQ. ID. NO: 3.
33. An anti-NKG2A antibody, or an antigen binding fragment thereof, according to any of embodiments 25-32, wherein the heavy chain of said antibody comprises SEQ. 1D. NO: 2 and the light chain of said antibody comprises SEQ. ID. NO: 3.
34. An anti-NKG2A antibody, or an antigen binding fragment thereof, according to any of embodiments 1-24, that competes with the antibody of any of embodiments 25-33 for binding to NKG2A.
35. An anti-NKG2A antibody, or an antigen binding fragment thereof, according to embodiment 25 or 26, wherein said antibody is humZ199.
36. An anti-NKG2A antibody, or an antigen binding fragment thereof, according to either of embodiments 25-26 or embodiment 35, wherein the heavy chain of said antibody comprises:
    a CRD1 sequence of amino acid residues 31 to 35 (SYAMS) of SEQ. ID. NO:4, wherein one or two of these amino acid residues may be substituted by a different amino acid residue; and/or
    a CRD2 sequence of amino acids 50-65 (EISSGGSYTYYADSVK) of SEQ. ID. NO: 4, wherein one, two, three or four of these amino acid residues may be substituted by a different amino acid residue; and/or
    a CDR3 sequence of amino acids 99-108 (HGDYPRFFDV) of SEQ. ID. NO: 4, wherein one, two or three of these amino acid residues may be substituted by a different amino acid.

37. An anti-NKG2A antibody, or an antigen binding fragment thereof, according to any of embodiments 25-26 or 35-36, wherein the light chain of said antibody comprises:
- a CDR1 sequence of amino acid residues 24-34 (SASSSVSSYIY) of SEQ. ID. NO: 5, wherein one, two or three of these amino acid residues may be substituted with a different amino acid; and/or
- a CDR2 sequence of amino acid residues 50-56 (LTSNLAS) of SEQ. ID. NO: 5, wherein one or two of these amino acid residues may be substituted with a different amino acid; and/or
- a CDR3 sequence of amino acid residues 89-97 (QQWSGNPYT) of SEQ. ID. NO: 5, wherein one, two or three of these amino acid residues may be substituted with a different amino acid.

38. An anti-NKG2A antibody, or an antigen binding fragment thereof, according to any of embodiments 25-26 or 35-37, wherein the heavy chain of said antibody comprises:
- a CRD1 sequence of amino acid residues 31 to 35 (SYAMS) of SEQ. ID. NO:4; and/or
- a CRD2 sequence of amino acids 50-65 (EISSGGSYTYYADSVK) of SEQ. ID. NO: 4; and/or
- a CDR3 sequence of amino acids –108 (HGDYPRFFDV) of SEQ. ID. NO: 4.

39. An anti-NKG2A antibody, or an antigen binding fragment thereof, according to any of embodiments 25-26 or 35-38, wherein the light chain of said antibody comprises:
- a CDR1 sequence of amino acid residues 24-34 (SASSSVSSYIY) of SEQ. ID. NO: 5; and/or
- a CDR2 sequence of amino acid residues 50-56 (LTSNLAS) of SEQ. ID. NO: 5; and/or
- a CDR3 sequence of amino acid residues –97 (QQWSGNPYT) of SEQ. ID. NO: 5.

40. An anti-NKG2A antibody, or an antigen binding fragment thereof, according to any of embodiments 25-26 or 35-39, wherein the heavy chain of said antibody comprises:
- a CRD1 sequence of amino acid residues 31 to 35 (SYWMN) of SEQ. ID. NO:2; and/or
- a CRD2 sequence of amino acids 50-59 (RIDPYDSETH) of SEQ. ID. NO: 2; and/or
- a CDR3 sequence of amino acids 95-102 (YCARGGYD) of SEQ. ID. NO: 2; and wherein the light chain of said antibody comprises:
- a CDR1 sequence of amino acid residues 24-34 (RASENIYSYLA) of SEQ. ID. NO: 3; and/or
- a CDR2 sequence of amino acid residues 50-56 (NAKTLAE) of SEQ. ID. NO: 3; and/or
- a CDR3 sequence of amino acid residues 89-97 (QHHYGTPRT) of SEQ. ID. NO: 3.

41. An anti-NKG2A antibody, or an antigen binding fragment thereof, according to any of embodiments 25-26 or 35-40, wherein the heavy chain of said antibody comprises SEQ. ID. NO: 4 and the light chain of said antibody comprises SEQ. ID. NO: 5.

42. An anti-NKG2A antibody, or an antigen binding fragment thereof, according to any of embodiments 1-25 that competes with the antibody of any of embodiments 35-41 for binding to NKG2A.

43. The use the anti-NKG2A antibody of any of the embodiments 1-7 or 13-42 for the treatment of cartilage destruction and/or bone erosion.

44. The use of the anti-NKG2A antibody of embodiment 43 for the treatment of a disease or disorder characterized by cartilage destruction and/or bone erosion.

45. The use of the anti-NKG2A antibody of embodiment 44, wherein the disease or disorder is osteoarthritis.

46. The use of the anti-NKG2A antibody of embodiment 44, wherein the disease or disorder is osteoporosis.

47. The use of the anti-NKG2A antibody of embodiment 44, wherein the disease or disorder is psoriatic arthritis.

48. The use of the anti-NKG2A antibody of embodiment 44, wherein the disease or disorder is rheumatic arthritis.

49. Method of treating a disease or disorder characterized by cartilage destruction and/or bone erosion, which comprises administering the anti-NKG2A antibody of any of the preceding embodiments to a patient.

50. Method of treating a disease or disorder characterized by cartilage destruction, which comprises administering the anti-NKG2A antibody of any of embodiments 1-49 to a patient.

51. Method of treating a disease or disorder characterized by bone erosion, which comprises administering the anti-NKG2A antibody of any of embodiments 1-49 to a patient.

52. Method of treating a disease of disorder characterized by cartilage destruction and bone erosion, which comprises administering the anti-NKG2A antibody of any of embodiments 1-49 to a patient.

53. An anti-NKG2A antibody, or an antigen binding fragment thereof, according to any of embodiments 1-49 for use as a medicament.

54. An anti-NKG2A antibody, or an antigen binding fragment thereof pharmaceutical formulation comprising the antibody according to any one of embodiments 1-49.

55. Use of the anti-NKG2A antibody, or an antigen binding fragment thereof, according to any one of embodiments 1-49 for the manufacture of a medicament.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

Unless otherwise expressly indicated or clearly contradicted by context, the term "or" herein is used in the inclusive sense of "and/or", and, accordingly, as implicitly providing support for an embodiment or aspect in which the term is to be interpreted in the exclusive sense of "either this or that".

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A method for treating cartilage destruction or bone erosion in a subject having osteoarthritis: comprising administering an anti-NKG2A antibody, or an antigen binding fragment thereof, to said subject, wherein said antibody blocks inhibitory signaling by CD94-NKG2A receptors and is a non-depleting antibody.

2. The method of claim 1, wherein said anti-NKG2A antibody stimulates selective elimination of cartilage destructive cells or reduces formation of bone eroding cells.

3. The method of claim 2, wherein the cartilage destructive cells are fibroblast-like synoviocytes (FLS).

4. The method of claim 2, wherein the bone eroding cells are osteoclasts.

5. A method for treating osteoarthritis, comprising administering an anti-NKG2A antibody, or an antigen binding fragment thereof, to a subject in need thereof, wherein said antibody blocks inhibitory signaling by CD94-NKG2A receptors and is a non-depleting antibody.

6. The method of claim 1, wherein the anti-NKG2A antibody is a humanized or human antibody.

7. The method of claim 6, wherein the anti-NKG2A antibody is humZ270 having a heavy chain comprising the amino acid sequence of SEQ ID NO: 2 and a light chain comprising the amino acid sequence of SEQ ID NO: 3.

8. The method of claim 1, wherein the heavy chain of said anti-NKG2A antibody comprises the CDR1, CDR2, and CDR3 of the heavy chain having the amino acid sequence of SEQ ID NO: 2 and the light chain of said anti-NKG2A antibody comprises the CDR1, CDR2, and CDR3 of the heavy chain having the amino acid sequence of SEQ ID NO: 3.

9. The method of claim 1, wherein said anti-NKG2A antibody or an antigen binding fragment thereof, competes with an antibody comprising a heavy chain comprising the CDR1, CDR2, and CDR3 of the heavy chain having the amino acid sequence of SEQ ID NO: 2 and the light chain of said anti-NKG2A antibody comprises the CDR1, CDR2, and CDR3 of the heavy chain having the amino acid sequence of SEQ ID NO: 3.

10. The method of claim 5, wherein the anti-NKG2A antibody is a humanized or human antibody.

11. The method of claim 10, wherein the anti-NKG2A antibody is humZ270 having a heavy chain comprising the amino acid sequence of SEQ ID NO: 2 and a light chain comprising the amino acid sequence of SEQ ID NO: 3.

12. The method of claim 5, wherein the heavy chain of said anti-NKG2A antibody comprises the CDR1, CDR2, and CDR3 of the heavy chain having the amino acid sequence of SEQ ID NO: 2 and the light chain of said anti-NKG2A antibody comprises the CDR1, CDR2, and CDR3 of the heavy chain having the amino acid sequence of SEQ ID NO: 3.

13. The method of claim 5, wherein said anti-NKG2A antibody or an antigen binding fragment thereof, competes with an antibody comprising a heavy chain comprising the CDR1, CDR2, and CDR3 of the heavy chain having the amino acid sequence of SEQ ID NO: 2 and the light chain of said anti-NKG2A antibody comprises the CDR1, CDR2, and CDR3 of the heavy chain having the amino acid sequence of SEQ ID NO: 3.

14. The method of claim 1, wherein said antibody is selected from the group consisting of an antibody comprising an IgG4 Fc domain and an antibody comprising a mutated Fc domain, wherein said mutation(s) results in reduced Fcγ receptor binding functions.

15. The method of claim 14, wherein said antibody comprises a mutated Fc domain, wherein said mutation(s) results in reduced Fcγ receptor binding functions.

16. The method of claim 5, wherein said antibody is selected from the group consisting of an antibody comprising an IgG4 Fc domain, and an antibody comprising a mutated Fc domain, wherein said mutation(s) results in reduced Fcγ receptor binding functions.

17. The method of claim 16, wherein said antibody comprises a mutated Fc domain, wherein said mutation(s) results in reduced Fcγ receptor binding functions.

18. The method of claim 1, wherein said antibody competes with the antibody having a heavy chain comprising the amino acid sequence of SEQ ID NO: 2 and a light chain comprising the amino acid sequence of SEQ ID NO: 3 for binding to NKG2A.

19. The method of claim 5, wherein said antibody competes with the antibody having a heavy chain comprising the amino acid sequence of SEQ ID NO: 2 and a light chain comprising the amino acid sequence of SEQ ID NO: 3 for binding to NKG2A.

* * * * *

UNITED STATES PATENT AND TRADEMARK OFFICE
CERTIFICATE OF CORRECTION

PATENT NO. : 9,512,228 B2
APPLICATION NO. : 14/124876
DATED : December 6, 2016
INVENTOR(S) : Kalle Soederstroem and Elisabeth Douglas Galsgaard It is certified that error appears in the above-identified patent and that said Letters Patent is hereby corrected as shown below:

In the Specification

Column 3,
Line 19, "suitable anti NKG2A anti-NKG2A antibodies." should read --suitable anti-NKG2A antibodies.--.

Column 4,
Line 15, "HLA-F." should read --HLA-E.--.
Lines 18-19, "express HLA E HLA-E." should read --express HLA-E.--.
Lines 22-23, "on RA FLS RA-FLS." should read --on RA-FLS.--.

Column 7,
Line 38, "(VII)" should read --(VH)--.

Column 11,
Line 57, "binding to a Ab to an Ab (also" should read --binding to an Ab (also--.

Column 12,
Lines 3-4, "conformational which" should read --conformational epitopes which--.

Column 16,
Line 3, "γ/γ T cells," should read --γ/δ T cells,--.

Column 17,
Line 8, "Hydroxvethyl" should read --Hydroxyethyl--.

Column 18,
Line 61, "(BASF)," should read --(RASF),--.

Signed and Sealed this
Twenty-fifth Day of July, 2017

Joseph Matal
*Performing the Functions and Duties of the
Under Secretary of Commerce for Intellectual Property and
Director of the United States Patent and Trademark Office*

Column 25,
Line 42, "NKp46 NK" should read --NKp46+ NK--.
Lines 46-47, "comparison). And Sections stained" should read --comparison). Sections stained--.

Column 30,
Line 42, "the 2199" should read --the Z199--.
Line 49, "(bars=100 Arrowheads" should read --(bars=100 μm). Arrowheads--.

Column 34,
Line 24, "antibody, binding" should read --antibody, or an antigen binding--.

Column 44,
Line 10, "Fe domain," should read --Fc domain,--.